United States Patent
Geffroy et al.

(10) Patent No.: US 11,819,563 B2
(45) Date of Patent: *Nov. 21, 2023

(54) AQUEOUS COSMETIC COMPOSITION COMPRISING ALKYLCELLULOSE

(75) Inventors: Nathalie Geffroy, Verrieres le Buisson (FR); Florence Levy, Paris (FR); Roberto Cavazzuti, Paris (FR)

(73) Assignee: L'OREAL, Paris (FR)

( * ) Notice: Subject to any disclaimer, the term of this patent is extended or adjusted under 35 U.S.C. 154(b) by 160 days.

This patent is subject to a terminal disclaimer.

(21) Appl. No.: 13/824,533

(22) PCT Filed: Sep. 19, 2011

(86) PCT No.: PCT/EP2011/066208
§ 371 (c)(1),
(2), (4) Date: Mar. 20, 2013

(87) PCT Pub. No.: WO2012/038374
PCT Pub. Date: Mar. 29, 2012

(65) Prior Publication Data
US 2013/0280197 A1    Oct. 24, 2013

Related U.S. Application Data

(60) Provisional application No. 61/425,272, filed on Dec. 21, 2010, provisional application No. 61/425,273, filed on Dec. 21, 2010, provisional application No. 61/425,263, filed on Dec. 21, 2010, provisional application No. 61/385,695, filed on Sep. 23, 2010, provisional application No. 61/385,682, filed on Sep. 23, 2010.

(30) Foreign Application Priority Data

| Sep. 20, 2010 | (FR) | 1057528 |
| Sep. 20, 2010 | (FR) | 1057530 |
| Dec. 16, 2010 | (FR) | 1060600 |
| Dec. 16, 2010 | (FR) | 1060650 |
| Dec. 16, 2010 | (FR) | 1060652 |

(51) Int. Cl.
*A61K 8/92* (2006.01)
*A61K 8/73* (2006.01)
*A61Q 19/00* (2006.01)
*A61Q 1/04* (2006.01)
*A61K 8/34* (2006.01)
*A61K 8/891* (2006.01)

(52) U.S. Cl.
CPC ............... *A61K 8/92* (2013.01); *A61K 8/342* (2013.01); *A61K 8/345* (2013.01); *A61K 8/731* (2013.01); *A61K 8/891* (2013.01); *A61Q 19/00* (2013.01); *A61Q 19/001* (2013.01); *A61Q 1/04* (2013.01)

(58) Field of Classification Search
CPC ....................................................... A61K 8/92
See application file for complete search history.

(56) References Cited

U.S. PATENT DOCUMENTS

| 2,230,063 A |   | 1/1941  | Klimist |
| 3,787,337 A | * | 1/1974  | Goodwin ..................... 252/545 |
| 4,683,134 A |   | 7/1987  | Palinczar |
| 4,699,779 A |   | 10/1987 | Palinczar |
| 4,797,273 A | * | 1/1989  | Linn ...................... A61K 8/064 424/59 |
| 5,641,493 A | * | 6/1997  | Date .................... A61K 8/0295 424/401 |
| 5,665,368 A |   | 9/1997  | Lentini et al. |
| 5,674,508 A | * | 10/1997 | Deserable ................ A61K 8/04 424/401 |
| 5,747,001 A | * | 5/1998  | Wiedmann ........... A61K 9/0078 424/45 |
| 5,747,013 A |   | 5/1998  | Mougin et al. |
| 5,849,834 A |   | 12/1998 | Matsuzaki et al. |
| 5,908,631 A |   | 6/1999  | Arnaud et al. |
| 6,001,374 A |   | 12/1999 | Nichols |
| 6,039,960 A |   | 3/2000  | Chung et al. |

(Continued)

FOREIGN PATENT DOCUMENTS

| DE | 31 12943 A1 | 10/1982 |
| DE | 698 32 545 T2 | 9/2006 |

(Continued)

OTHER PUBLICATIONS

Wikipedia, Hydrocarbon, (accessed Feb. 26, 2015), pp. 1-5.*
Wikipedia Triethanolamine, (acessed Feb. 26, 2015), pp. 1-6.*
SAAPedia, Octyldodecyl stearoyl stearate (Oct. 28, 2014), pp. 1-2.*
European Food Safety Authority, Mineral OII Hydrocarbon, (Jun. 6, 2012) pp. 1-2 (Year: 2012).*
Chemical Book, Mineral Oil, pp. 1-2, (Nov. 20, 2018). (Year: 2018).*
Love to Know Makeup (Jun. 11, 2008), pp. 1-4. (Year: 2008).*
Chemical Land, Dihydroxyacetone, acessed Jun. 6, 2019, pp. 1-2 (Year: 2019).*

(Continued)

*Primary Examiner* — Andrew S Rosenthal
*Assistant Examiner* — Lyndsey M Beckhardt
(74) *Attorney, Agent, or Firm* — Oblon, McClelland, Maier & Neustadt, L.L.P.

(57) ABSTRACT

A cosmetic composition includes, in a physiologically acceptable medium: at least water, at least alkylcellulose, at least one first hydrocarbon-based non-volatile oil, chosen from: C10-C26 alcohols, preferably monoalcohols; optionally hydroxylated monoesters, diesters or triesters of a C2-C8 monocarboxylic or polycarboxylic acid and of a C2-C8 alcohol; esters of a C2-C8 polyol and of one or more C2-C8 carboxylic acids. At least one second non-volatile oil chosen from silicone oils and/or fluoro oils or hydrocarbon-based oils other than the said first oil; at least one stabilizer chosen from surfactants and/or hydrophilic gelling agents, preferably chosen from associative polymers, natural polymers and their mixture.

17 Claims, No Drawings

(56) References Cited

U.S. PATENT DOCUMENTS

| | | | |
|---|---|---|---|
| 6,387,405 B1* | 5/2002 | Shah et al. | 424/486 |
| 2002/0015683 A1 | 2/2002 | Nichols et al. | |
| 2002/0022009 A1 | 2/2002 | De La Poterie et al. | |
| 2002/0127192 A1* | 9/2002 | Murphy | A61K 8/02 424/64 |
| 2003/0077962 A1* | 4/2003 | Krzysik | A61K 8/0208 442/100 |
| 2004/0081633 A1 | 4/2004 | Mercier et al. | |
| 2005/0244442 A1 | 11/2005 | Sabino et al. | |
| 2005/0276763 A1 | 12/2005 | Pfeifer et al. | |
| 2006/0013789 A1* | 1/2006 | Blin et al. | 424/70.12 |
| 2006/0019848 A1 | 1/2006 | Luo et al. | |
| 2006/0275226 A1* | 12/2006 | Dahms | A61K 8/06 424/59 |
| 2009/0004252 A1* | 1/2009 | Lowndes | A61P 17/00 424/443 |
| 2009/0098068 A1* | 4/2009 | Takakura | A61K 8/19 424/59 |
| 2011/0038820 A1 | 2/2011 | Barba et al. | |

FOREIGN PATENT DOCUMENTS

| | | |
|---|---|---|
| EP | 0 336 902 A2 | 10/1989 |
| EP | 0 795 318 A2 | 9/1997 |
| EP | 0 823 250 A2 | 2/1998 |
| EP | 0 861 657 A2 | 9/1998 |
| EP | 1 051 968 A2 | 11/2000 |
| EP | 1 192 937 A2 | 4/2002 |
| EP | 1192937 A2 | 4/2002 |
| EP | 1 604 635 A2 | 12/2005 |
| EP | 1 604 644 A1 | 12/2005 |
| EP | 1 913 929 | 4/2008 |
| EP | 2 116 221 A1 | 11/2009 |
| EP | 2 599 472 B1 | 11/2016 |
| FR | 2 771 628 A1 | 6/1999 |
| FR | 2 771 629 A1 | 6/1999 |
| FR | 2 918 272 A1 | 1/2009 |
| FR | 2 921 266 B1 | 6/2012 |
| FR | 2 978 037 B1 | 1/2014 |
| GB | 795841 | 5/1958 |
| JP | H10-067624 A | 3/1998 |
| JP | 2000-219617 A | 8/2000 |
| KR | 10-2010-0103708 A | 9/2010 |
| WO | WO 96/36310 A1 | 11/1996 |
| WO | WO 2005/046626 A2 | 5/2005 |
| WO | WO 2006/017203 A1 | 2/2006 |
| WO | 2007/026101 A1 | 3/2007 |
| WO | 2009/006218 A2 | 1/2009 |
| WO | WO 2009/080953 | 7/2009 |
| WO | WO 2009/080958 A2 | 7/2009 |
| WO | 2009/105294 A2 | 8/2009 |
| WO | WO 2012/038879 A2 | 3/2012 |
| WO | WO 2012/064714 A2 | 5/2012 |
| WO | WO 2013/088051 A2 | 6/2013 |
| WO | WO 2013/102727 A1 | 7/2013 |

OTHER PUBLICATIONS

"Smooth Cover Gel," Database GNPD [Online] Mintel, Sep. 2009, XP-002658176, pp. 1-2.
"Mousse Foundation Natural Bronzing Effect," Database GNPD [Online] Mintel, Nov. 2010, XP-002658177, pp. 1-2.
"Ceramide Moisture Network Night Cream [Ingredients]," Database GNPD [Online] Mintel, Sep. 2004, XP-002658178.
"Beauty Body Gel," Database GNPD [Online] Mintel, Sep. 2010, XP-002658179, pp. 1-2.
"Butter Shine Lipstick," Database GNPD [Online] Mintel, Oct. 2008, XP-002658180, pp. 1-2.
"Lip Polish," Database GNPD [Online] Mintel, Jun. 2000, XP-002658181, pp. 1-7.
"Liquid Foundation," Database GNPD [Online] Sep. 2010, XP-002658182, pp. 1-4.
May 6, 2011 French Search Report and Written Opinion issued in French Patent Application No. FR 1057526 (with translation).
May 6, 2011 French Search Report and Written Opinion issued in French Patent Application No. FR 1057528 (with translation).
Sep. 5, 2011 French Search Report and Written Opinion issued in French Patent Application No. FR 1060600 (with translation).
Sep. 5, 2011 French Search Report and Written Opinion issued in French Patent Application No. FR 1060650 (with translation).
Sep. 5, 2011 French Search Report and Written Opinion issued in French Patent Application No. FR 1060652 (with translation).
Apr. 3, 2012 Written Opinion of the International Searching Authority issued in International Application No. PCT/IB2011/054087.
Mar. 26, 2013 International Preliminary Report on Patentability issued in International Application No. PCT/IB2011/054087.
Apr. 3, 2012 International Search Report issued in International Application No. PCT/IB2011/054087.
Oct. 31, 2012 Written Opinion issued in French Patent Application 1250017.
Mar. 10, 2014 Office Action issued in U.S. Appl. No. 13/824,548.
Feb. 13, 2014 Office Action issued in U.S. Appl. No. 13/824,548.
Oct. 31, 2012 French Search Report issued in French Patent Application 1250017 (with translation).
U.S. Appl. No. 14/370,355, filed Jul. 2, 2014.
U.S. Appl. No. 13/824,548, filed Jul. 10, 2013.
International Search Report issued in International Patent Application No. PCT/EP2011/066208 dated Mar. 29, 2012.
International Preliminary Report on Patentability issued in International Patent Application No. PCT/EP2011/066208 dated Mar. 26, 2013.
XP-002658180, Mintel, Butter Shine Lipstick, Clinique, Oct. 2008.
Melzer, Eva et al., "Ethylcellulose: a new type of emulsion stabilizer," European Journal of Pharmaceutics and Biopharmaceuticals, 56:23-27, 2003.
"Making Emulsions for Cosmetics," makingcosmetics.com, Oct. 12, 2004.
Google search results for "cosmetic and emulsion," Nov. 30, 2014.
Dec. 18, 2014 Office Action issued in U.S. Appl. No. 13/824,548.
Dec. 24, 2014 Office Action issued in Japanese Application No. 2013-528824.
Flirt-Tinis Protective Lip Balm, XP-002731953, Sep. 2008, pp. 1-3.
Tendertones SPF12 (Purring), XP-002731954, Aug. 2007, pp. 1-2.
Lip Moisture Cream SPF 30, XP-002731955, Apr. 2006, pp. 1-3.
Nov. 13, 2014 Search Report and Written Opinion issued in French Application No. 1452985.
Nov. 14, 2013 Office Action issued in Korean Application No. 10-2013-7018815.
Nov. 28, 2013 Office Action issued in Korean Application No. 10-2013-7021162.
Mar. 10, 2015 Office Action issued in Chinese Application No. 201180055831.3.
Arbonne product "Lip Polish".
Why balsam and vanishing cream in the cosmetics are classified as "water-in-oil" type and a "oil-in-water" type?
Mar. 11, 2016 Office Action issued in U.S. Appl. No. 13/824,548.
Mar. 31, 2016 Office Action issued in U.S. Appl. No. 14/370,335.
"Colour Gloss Extension", Clarins, Product No. 10116327, Aug. 2002.
McLain; "Final Report of the Cosmetic Ingredient Review Expert Panel on the Safety Assessment of Polyisobutene and Hydrogenated Polyisobutene as Used in Cosmetics," International Journal of Toxicology, 27 (Suppl. 4): 83-106, 2008.
Oct. 8, 2015 Office Action issued in U.S. Appl. No. 14/370,335.
Susan C. Smolinske "Handbook of Food, Drug, and Cosmetic Excipients" CRC Press LLC, 1992, p. 231 (with cover pages).
"Glossy Full Couleur Extreme Shine Lip Gloss", Make Up for Ever, Product No. 1522027, Mar. 2011, 3 pages.
Marie Contier et al., "Characterization of the tack and gloss of cosmetic formulations", LVMH Recherche Parfums & Cosmetiques Materials Innovation Department, May 13, 2016, pp. 1-5 (with English translation).
Written Opinion dated Jul. 21, 2008 in French Patent Application No. 0854940.

(56) References Cited

OTHER PUBLICATIONS

"Basic Properties of Parleam™", NOF Corporation Oleo & Specialty Chemicals Div., Apr. 2015, 2 pages.

"Report on tests carried out by the company L'Oréal in response to the notice of opposition formed by the company Parfums Christian Dior against patent EP 2 618 803 B1", L'Oréal, Jun. 19, 2017, pp. 1-3 (with English translation).

"Ethocel", Ethylcellulose Polymers Technical Handbook, Dow Cellulosics, Sep. 2005, pp. 1-28.

Charles M. Hansen, "The Three Dimensional Solubility Paramater—Key to Paint Component Affinities: I. Solvents, Plasticizers, Polymers, and Resins", Jouranl of Paint Technology, vol. 39, No. 505, Feb. 1967, pp. 104-117.

Notice of Opposition dated Jan. 6, 2017 in European Patent Application No. 2 618 803 B1 (with English translation).

Response to Notice of Opposition dated Jun. 19, 2017 in European Patent Application No. 2 618 803 (with English translation).

Oct. 21, 2015 Notice of Opposition issued in European Application No. 2 618 811.

\* cited by examiner

AQUEOUS COSMETIC COMPOSITION COMPRISING ALKYLCELLULOSE

The present invention is directed towards proposing cosmetic compositions comprising alkylcellulose, which are intended in particular for making up and/or caring for the lips or the skin, especially the lips, which are capable of producing a deposit, especially a makeup deposit, which shows good cosmetic properties, especially in terms of comfort, absence of tackiness and gloss.

The compositions targeted according to the invention are more specifically aqueous compositions, which are particularly appreciated for formulating water-soluble dyestuffs.

In general, cosmetic compositions need to afford an aesthetic effect when applied to the skin and/or the lips, and to maintain this aesthetic effect over time.

In fact, the production of an aesthetic effect, after applying a cosmetic composition, results from an assembly of properties intrinsic to the composition which are expressed in terms of makeup performance, cosmetic properties such as comfort on application and on wearing, makeup precision, makeup uniformity, gloss and/or wear property of the gloss over time.

In particular, producing a homogeneous composition that is stable over time, and improving the gloss and/or the wear property over time of cosmetic products, once applied to the skin or the lips, is an ongoing concern of formulators working in the field of lipsticks, in stick form or in gloss form for the lips, and other skincare and/or lipcare products.

Ethylcellulose is already known for its capacity, when it is dissolved in sufficient amount in cosmetic and/or therapeutic compositions, to improve the adherence and the wear property of the resulting films. It has also been demonstrated that ethylcellulose dissolved in sufficient amount in compositions makes it possible, by virtue of its properties as a film-forming agent, to facilitate the formation of a film on the skin and/or the lips, and to improve the water resistance of this film.

Unfortunately, ethylcellulose, and alkylcelluloses in general (with an alkyl group comprising from 1 to 6 carbon atoms), is of limited solubility in the majority of the solvents commonly used in cosmetic and/or dermatological formulations. In general, monoalcohols containing from 2 to 8 carbon atoms, such as ethanol, butanol, methanol or isopropanol, are preferred for dissolving sufficient amounts of ethylcellulose in cosmetic or pharmaceutical compositions. Evaporation of the $C_2$-$C_8$ monoalcohols leads, after application of the corresponding cosmetic composition to the skin or the lips, firstly to concentration of the deposit and secondly to the formation of a coat on the surface of the skin or the lips that has a very good wear property. For example, document WO 96/36310 proposes cosmetic compositions especially comprising ethylcellulose dissolved in ethyl alcohol (SDA 38B-190 or SDA 40B-190 solvents).

However, these volatile monoalcohols have the drawback of being potentially irritant to the skin and/or the lips, and consequently may prove to be detrimental in the case of repeated use on the skin.

In order to overcome this problem, it has been proposed in document U.S. Pat. No. 5,908,631 to use, as an alternative to $C_2$-$C_8$ monoalcohols, a certain number of solvents for ethylcellulose, such as lanolin oil, certain triglycerides, certain propylene glycol or neopentyl glycol esters, isostearyl lactate, and mixtures thereof.

Unfortunately, replacing these $C_2$-$C_8$ monoalcohols, which are volatile compounds, with these non-volatile solvents may on the other hand prove to be detrimental in terms of comfort and of tackiness of the resulting deposit.

Consequently, there is still a need for cosmetic compositions, which are free of $C_2$-$C_8$ monoalcohols, comprising a sufficient amount of alkylcellulose, and which are capable of forming on the skin and/or the lips a deposit that has gloss and comfort properties and that is not tacky.

In the context of caring for the lips, it is more particularly desirable to introduce into lipstick compositions active agents such as moisturizers, for example in order to contribute toward moisturizing the lips and for the wear comfort of the deposit. However, lipstick formulations (whether they are solid or liquid) are generally anhydrous, and the introduction of active agents such as glycerol, for example, is the cause of stability problems of the composition (exudation). The introduction of water into standard architectures causes problems of instability over time of the compositions (i.e. they show phase separation or exudation phenomena).

There is more particularly a need for compositions for making up and/or caring for the skin and/or the lips, comprising a sufficient amount of alkylcellulose, which are homogeneous and stable over time (which do not form grains and do not undergo phase separation), which are easy to apply, which allow the production of a thin, light, uniform, glossy and comfortable deposit that, in particular, is sparingly tacky or non-tacky, and which, in certain embodiments, have a satisfactory level of wear property.

The object of the present invention is, precisely, to satisfy these needs.

As emerges from the examples presented below, the inventors have discovered that the abovementioned expectations can be satisfied by formulating the alkylcellulose in the form of a dispersion in water with a mixture of specific oils other than $C_2$-$C_8$ monoalcohols.

Thus, according to a first of its aspects, a subject of the present invention is a cosmetic composition comprising, in a physiologically acceptable medium:
- at least water, in particular at least 5% by weight of water,
- at least alkylcellulose,
- at least a first hydrocarbon-based non-volatile oil, chosen from:
  - $C_{10}$-$C_{26}$ alcohols, preferably monoalcohols, in particular $C_{16}$-$C_{26}$ branched monoalcohols;
  - optionally hydroxylated monoesters, diesters or triesters of a $C_2$-$C_8$ monocarboxylic or polycarboxylic acid and of a $C_2$-$C_8$ alcohol;
  - esters of a $C_2$-$C_8$ polyol and of one or more $C_2$-$C_8$ carboxylic acids.
- at least one second non-volatile oil chosen from silicone oils and/or fluoro oils or hydrocarbon-based oils other than the said first oil;
- at least one stabilizer chosen from surfactants and/or hydrophilic gelling agents, in particular chosen from associative polymers, natural polymers, and their mixture.

In a particular embodiment, a subject of the present invention is a cosmetic composition comprising, in a physiologically acceptable medium:
- at least water, in particular at least 5% by weight of water,
- at least alkylcellulose,
- at least a first hydrocarbon-based non-volatile oil, chosen from:
  - $C_{10}$-$C_{26}$ alcohols, preferably monoalcohols, in particular $C_{16}$-$C_{26}$ branched monoalcohols;
  - optionally hydroxylated monoesters, diesters or triesters of a $C_2$-$C_8$ monocarboxylic or polycarboxylic acid and of a $C_2$-$C_8$ alcohol;

esters of a $C_2$-$C_8$ polyol and of one or more $C_2$-$C_8$ carboxylic acids.

at least one second non-volatile oil chosen from silicone oils and/or fluoro oils or hydrocarbon-based oils other than the said first oil;

at least one stabilizer chosen from surfactants and/or hydrophilic gelling agents, in particular chosen from associative polymers, natural polymers, and their mixture, the said composition comprising at least sodium lauryl sulphate and optionally an additional non ionic or anionic surfactant.

According to one particular embodiment of the invention, a cosmetic composition according to the invention also comprises at least one silicone gum.

According to one particular embodiment, a cosmetic composition according to the invention also comprises at least one organopolysiloxane elastomer.

According to yet another particular embodiment, a composition according to the invention also comprises at least one silicone resin.

According to yet another particular embodiment, a composition according to the invention also comprises at least one active agent chosen from moisturizers, cicatrizing agents and antiaging agents.

Advantageously, a cosmetic composition according to the invention is homogeneous, stable (no exudation or phase separation) over time (especially after 1 month at room temperature), easy to apply to the skin and/or the lips, and produces a uniform deposit that shows good properties in terms of gloss, comfort (the deposit is thin and light) and is non-tacky or sparingly tacky, and, in certain embodiments, contributes toward caring for the lips.

In particular, in the context of a composition for caring for the lips, since the composition according to the invention comprises water, this water lends itself particularly to the introduction of hydrophilic active agents into the composition, in particular without any problem of stability of the composition and/or of the active agent.

Moreover, since the deposit on the lips of a composition according to the invention shows a good level of wear property, this ensures the remanence of the active agent on the lips and thus improves the care efficacy (moisturizing, cicatrizing and/or antiaging effect) on the lips.

Advantageously, a composition according to the invention is easy to apply, and can lead to precise application of makeup to the contours of the lips.

A composition according to the invention also proves to be particularly suitable for the use of water-soluble dyes.

As emerges from the examples below, the combination of the oils under consideration according to the invention proves to be particularly advantageous for formulating alkylcelluloses, preferably such as ethylcellulose, in the said composition.

A composition according to the invention advantageously allows the use of an effective amount of alkylcellulose. For the purposes of the present invention, the term "effective amount" means an amount that is sufficient to obtain the expected effect, as described previously.

In particular, a composition according to the invention comprises at least 1% and particularly preferably at least 4% by weight (solids) of alkylcellulose (preferentially ethylcellulose) relative to the total weight of the composition.

Particularly preferably, the composition according to the invention comprises from 4% to 60% by weight of alkylcellulose (preferably ethylcellulose), more preferably from 5% to 30% by weight and more preferably still from 5% to 20% by weight, relative to the total weight of the composition.

The term "physiologically acceptable medium" is intended to denote a medium that is particularly suitable for the application of a composition according to the invention to the skin and/or the lips.

Preferably, the composition according to the invention is liquid.

The term "liquid" means a composition that is capable of flowing under its own weight, at room temperature (20° C.) and at atmospheric pressure (760 mmHg), as opposed to "solid" compositions.

A composition according to the invention is preferably in the form of an emulsion of oil in an aqueous phase.

Preferably, the cosmetic composition according to the invention is a liquid lipstick, for instance a gloss.

According to one particular embodiment, a composition of the invention comprises less than 5% by weight of silicone surfactant(s), in particular less than 4% by weight, especially less than 3% by weight, more particularly less than 2% by weight and in particular less than 1% by weight, or even is totally free of silicone surfactant.

According to another of its aspects, a subject of the present patent application is a cosmetic process for making up and/or caring for the lips and/or the skin, in particular the lips, comprising at least one step that consists in applying to the lips and/or the skin at least one composition as defined previously.

In particular, a subject of the present patent application is a cosmetic process for making up and/or caring for the lips, comprising at least one step that consists in applying to the lips at least one cosmetic composition comprising, in a physiologically acceptable medium:

at least water, in particular at least 5% by weight of water, at least alkylcellulose, at least a first hydrocarbon-based non-volatile oil, chosen from:

$C_{10}$-$C_{26}$ alcohols, preferably monoalcohols, in particular $C_{16}$-$C_{26}$ monoalcohols;

optionally hydroxylated monoesters, diesters or triesters of a $C_2$-$C_8$ monocarboxylic or polycarboxylic acid and of a $C_2$-$C_8$ alcohol;

esters of a $C_2$-$C_8$ polyol and of one or more $C_2$-$C_8$ carboxylic acids.

at least one second non-volatile oil chosen from silicone oils and/or fluoro oils or hydrocarbon-based oils other than the said first oil;

at least one stabilizer chosen from surfactants and/or hydrophilic gelling agents, in particular chosen from associative polymers, natural polymers, and their mixture.

Ethylcellulose

A composition according to the invention comprises at least alkylcellulose, the alkyl residue of which comprises between 1 and 6 carbon atoms and preferably between 1 and 3 carbon atoms, preferably ethylcellulose.

According to one particularly preferred embodiment, the alkylcellulose (preferentially ethylcellulose) is present in a composition according to the invention in a content (solids) greater than or equal to 4% by weight and in particular ranging from 1% to 60% by weight.

Particularly preferably, the composition according to the invention comprises from 4% to 60% by weight of alkylcellulose, more preferably from 5% to 30% by weight and more preferably still from 5% to 20% by weight, relative to the total weight of the said composition.

The alkylcellulose is a cellulose alkyl ether comprising a chain formed from β-anhydroglucose units linked together via acetal bonds. Each anhydroglucose unit contains three replaceable hydroxyl groups, all or some of these hydroxyl groups being able to react according to the following reaction:

RONa+C$_2$H$_5$Cl→ROC$_2$H$_5$+NaCl, in which R represents a cellulose radical.

Advantageously, the alkylcellulose is chosen from methylcellulose, ethylcellulose and propylcellulose.

According to one particularly preferred embodiment, the alkylcellulose is ethylcellulose.

It is a cellulose ethyl ether.

Total substitution of the three hydroxyl groups would lead for each anhydroglucose unit to a degree of substitution of 3, in other words to a content of alkoxy groups of 54.88%

The ethylcellulose polymers used in a cosmetic composition according to the invention are preferentially polymers with a degree of substitution with ethoxy groups ranging from 2.5 to 2.6 per anhydroglucose unit, in other words comprising a content of ethoxy groups ranging from 44% to 50%.

According to a preferred mode, the alkylcellulose (preferably ethylcellulose) is used in a composition of the invention in the form of particles dispersed in an aqueous phase, like a dispersion of latex or pseudolatex type. The techniques for preparing these latex dispersions are well known to those skilled in the art.

The product sold by the company FMC Biopolymer under the name Aquacoat ECD-30, which consists of a dispersion of ethylcellulose at a rate of about 26.2% by weight in water and stabilized with sodium lauryl sulfate and cetyl alcohol, is most particularly suitable for use as an aqueous dispersion of ethylcellulose.

According to one particular embodiment, the aqueous dispersion of ethylcellulose, in particular the product Aquacoat ECD, may be used in a proportion of from 3% to 90% by weight, in particular from 10% to 60% by weight and preferably from 20% to 50% by weight of ethylcellulose dispersion relative to the total weight of the composition.

According to one particularly preferred embodiment, the composition of the invention thus comprises at least one surfactant chosen from anionic and nonionic surfactants, in particular as described more precisely hereinbelow, and especially from anionic surfactants such as sodium lauryl sulfate.

These surfactants may be introduced more particularly, at least partly, by the aqueous dispersion of alkylcellulose used in the preparation of a composition of the invention.

Thus, according to another of its aspects, the present invention also relates to a process for preparing a composition according to the invention, characterized in that the alkylcellulose is used therein in the form of a stable aqueous dispersion of alkylcellulose, said dispersion especially comprising at least one surfactant chosen from anionic and nonionic surfactants.

As mentioned previously, the alkylcellulose, preferably in the form of a stable aqueous dispersion of alkylcellulose, is used according to the present invention in combination with a mixture of oils as described more particularly hereinbelow.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition of the invention to the skin and/or the lips, for instance water, the oils or organic solvents commonly used in cosmetic compositions.

The physiologically acceptable medium (acceptable tolerance, toxicology and feel) is generally adapted to the nature of the support onto which the composition is to be applied, and also to the form in which the composition is to be conditioned.

Fatty Phase

The composition according to the invention comprises at least one fatty phase and especially a liquid fatty phase, at least a first specific hydrocarbon-based non-volatile oil and at least a second non-volatile oil chosen from silicone oils and/or fluoro oils or hydrocarbon-based oils other than the said first oil. The term "oil" means a non-aqueous water-immiscible compound, which is liquid at room temperature (25° C.) and atmospheric pressure (760 mmHg).

Specific First Hydrocarbon-Based Non-Volatile Oil

The composition according to the invention comprises one or more first hydrocarbon-based non-volatile oil(s), chosen from:
   $C_{10}$-$C_{26}$ alcohols, preferably monoalcohols; in particular $C_{16}$-$C_{26}$ branched monoalcohols;
   optionally hydroxylated monoesters, diesters or triesters of a $C_2$-$C_8$ monocarboxylic or polycarboxylic acid and of a $C_2$-$C_8$ alcohol;
   esters of a $C_2$-$C_8$ polyol and of one or more $C_2$-$C_8$ carboxylic acids.

The term "non-volatile" refers to an oil whose vapour pressure at room temperature and atmospheric pressure is non-zero and less than 0.02 mmHg (2.66 Pa) and better still less than $10^{-3}$ mmHg (0.13 Pa).

Preferably, the said "second oil" is chosen from:
   $C_{10}$-$C_{26}$ monoalcohols; in particular $C_{16}$-$C_{26}$ branched monoalcohols; optionally hydroxylated monoesters of a $C_2$-$C_8$ carboxylic acid and of a $C_2$-$C_8$ alcohol;
   optionally hydroxylated diesters of a $C_2$-$C_8$ dicarboxylic acid and of a $C_2$-$C_8$ alcohol;
   optionally hydroxylated triesters of a $C_2$-$C_8$ tricarboxylic acid and of a $C_2$-$C_8$ alcohol;
   esters of a $C_2$-$C_8$ polyol and of one or more $C_2$-$C_8$ carboxylic acids.

The term "hydrocarbon-based oil" means an oil formed essentially from, constituted by, carbon and hydrogen atoms, and possibly oxygen atoms, and free of heteroatoms such as N, Si, F and P. The hydrocarbon-based oil is thus different from a silicone oil or a fluoro oil.

In the present case, the said first oils comprise at least one oxygen atom.

In particular, the said first non-volatile hydrocarbon-based oil comprises at least one alcohol function (it is then an "alcohol oil") and/or at least one ester function (it is then an "ester oil").

The ester oils that may be used in the compositions according to the invention may especially be hydroxylated.

According to one particular embodiment, a composition according to the invention comprises one or more first non-volatile hydrocarbon-based oil(s) in a content ranging from 5% to 75%, in particular from 10% to 50% by weight and preferably from 20% to 45% by weight relative to its total weight.

According to one particularly preferred embodiment, the non-volatile hydrocarbon-based oil and the alkylcellulose (in particular ethylcellulose) are used in the composition according to the invention in a "non-volatile hydrocarbon-based first oil(s)/alkylcellulose" weight ratio of between 1 and 20 and preferably between 2 and 15. Particularly preferably, the "non-volatile hydrocarbon-based first oil(s)/alkylcellulose" weight ratio is between 3 and 10.

More particularly, the non-volatile hydrocarbon-based first oil used in a composition according to the invention may especially have plasticizing properties, i.e. it can impart suppleness and comfort to the deposit formed with the composition according to the invention.

According to one particularly preferred embodiment, the said first oil is a $C_{10}$-$C_{26}$ alcohol, preferably a monoalcohol.

Preferably, the $C_{10}$-$C_{26}$ alcohols are saturated or unsaturated, and branched or unbranched, and comprise from 10 to 26 carbon atoms. Preferably, the $C_{10}$-$C_{26}$ alcohols are fatty alcohols.

As examples of fatty alcohols that may be used according to the invention, mention may be made of linear or branched fatty alcohols, of synthetic origin or alternatively of natural origin, for instance alcohols derived from plant material (coconut, palm kernel, palm, etc.) or animal material (tallow, etc.). Needless to say, other long-chain alcohols may also be used, for instance ether alcohols or Guerbet alcohols. Finally, use may also be made of certain more or less long fractions of alcohols of natural origin, for instance coconut ($C_{12}$ to $C_{16}$) or tallow ($C_{16}$ to $C_{18}$) or compounds of diol or cholesterol type.

Use is preferably made of a fatty alcohol comprising from 10 to 24 carbon atoms and more preferentially from 12 to 22 carbon atoms.

As particular examples of fatty alcohols that may be used in the context of the present invention, mention may be made especially of lauryl alcohol, myristyl alcohol, cetyl alcohol, stearyl alcohol, isostearyl alcohol, palmityl alcohol, oleyl alcohol, cetearyl alcohol (mixture of cetyl alcohol and stearyl alcohol), behenyl alcohol, erucyl alcohol, arachidyl alcohol, 2-hexyldecyl alcohol, isocetyl alcohol and octyldodecanol, and mixtures thereof.

Preferably, the said "first oil" is octyldodecanol.

According to a second embodiment, the said first oil is an ester oil chosen from:
optionally hydroxylated monoesters of a $C_2$-$C_8$ carboxylic acid and of a $C_2$-$C_8$ alcohol;
optionally hydroxylated diesters of a $C_2$-$C_8$ dicarboxylic acid and of a $C_2$-$C_8$ alcohol; such as diisopropyl adipate, 2-diethylhexyl adipate, dibutyl adipate or diisostearyl adipate,
optionally hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate,
esters of a $C_2$-$C_8$ polyol and of one or more $C_2$-$C_8$ carboxylic acids, such as glycol diesters of monoacids, such as neopentyl glycol diheptanoate, or glycol triesters of monoacids, such as triacetin.

Second Non-Volatile Silicone Oil and/or Fluoro Oil or Hydrocarbon-Based Oil Other than the Said First Oil According to one of its aspects, a composition according to the invention comprises at least a second non-volatile oil chosen from silicone oils and/or fluoro oils or hydrocarbon-based oils other than the said first oil.

The term "non-volatile" refers to an oil whose vapour pressure at room temperature and atmospheric pressure is non-zero and less than 0.02 mmHg (2.66 Pa) and better still less than $10^{-3}$ mmHg (0.13 Pa).

Preferably, the non-volatile oil(s) chosen from silicone oils and/or fluoro oils or hydrocarbon-based oil other than the said first oil are present in a total content ranging from 5% to 75% by weight, preferably from 10% to 40% by weight or alternatively from 15% to 30% by weight relative to the total weight of the said composition.

According to one particular embodiment, a composition according to the invention comprises one or more non-volatile silicone oils (preferably phenyl silicone oils) and/or non-volatile fluoro oils or hydrocarbon-based oil other than the said first oil, in a proportion of at least 5% by weight relative to the total weight of the composition, especially from 5% to 75% by weight and particularly preferably from 10% to 45% by weight.

According to one particularly preferred embodiment, the composition comprises a total content of non-volatile oils (i.e. all the non-volatile oils of the composition, irrespective of their nature) of between 40% and 80% by weight and preferably between 45% and 75% by weight relative to the total weight of the composition.

According to a particularly preferred embodiment, the non-volatile oils (i.e. all the non-volatile oils of the composition, irrespective of their nature) and the alkylcellulose are used in the composition according to the invention in a non-volatile oil(s)/alkylcellulose weight ratio of between 1 and 20 and preferably between 4 and 15.

According to one preferred embodiment, the said second oil is chosen from silicone oils and/or fluoro oils.

Non-Volatile Silicone Oil

According to a first preferred embodiment, the non-volatile oil is a silicone oil.

The term "silicone oil" means an oil comprising at least one silicon atom.

The non-volatile silicone oil that may be used in the invention may be chosen especially from silicone oils especially with a viscosity at 25° C. of greater than or equal to 9 centistokes (cSt) ($9 \times 10^{-6}$ m$^2$/s) and less than 800 000 cSt, preferably between 50 and 600 000 cSt and preferably between 100 and 500 000 cSt. The viscosity of this silicone oil may be measured according to standard ASTM D-445.

According to a first embodiment, the non-volatile silicone oil is a non-phenyl silicone oil.

The non-volatile non-phenyl silicone oil may be chosen from:
non-volatile polydimethylsiloxanes (PDMS),
PDMSs comprising alkyl or alkoxy groups, which are pendent and/or at the end of the silicone chain, these groups each containing from 2 to 24 carbon atoms,
PDMSs comprising aliphatic and/or aromatic groups, or functional groups such as hydroxyl, thiol and/or amine groups,
polyalkylmethylsiloxanes optionally substituted with a fluoro group, such as polymethyltrifluoropropyldimethylsiloxanes,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

According to one embodiment, a composition according to the invention contains at least one non-phenyl silicone oil, in particular such as a linear (i.e. non-cyclic) oil.

Representative examples of these non-volatile non-phenyl linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

When the nonvolatile silicone oil is a dimethicone, it is more particularly present in a content of greater than or equal to 5% by weight relative to the total weight of said composition.

Such a content makes it possible in particular to obtain the desired gloss effect.

The non-phenyl silicone oil may be chosen especially from the silicones of formula (I):

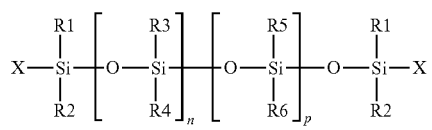

(I)

in which:
- $R_1$, $R_2$, $R_5$ and $R_6$ are, together or separately, an alkyl radical containing 1 to 6 carbon atoms,
- $R_3$ and $R_4$ are, together or separately, an alkyl radical containing from 1 to 6 carbon atoms, a vinyl radical, an amine radical or a hydroxyl radical,
- X is an alkyl radical containing from 1 to 6 carbon atoms, a hydroxyl radical or an amine radical,
- n and p are integers chosen so as to have a fluid compound, in particular whose viscosity at 25° C. is between 9 centistokes (cSt) ($9 \times 10^{-6}$ m$^2$/s) and 800 000 cSt.

As non-volatile silicone oils that may be used according to the invention, mention may be made of the compounds of formula (I) for which:
- the substituents $R_1$ to $R_6$ and X represent a methyl group, and p and n are such that the viscosity is 500 000 cSt, such as the product sold under the name SE30 by the company Général Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
- the substituents $R_1$ to $R_6$ and X represent a methyl group, and p and n are such that the viscosity is 350 cSt, such as the product sold under the name Dow Corning 200 Fluid 350 CS by the company Dow Corning, or under the name Wacker-Belsil DM 350 by the company Wacker,
- the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to a second embodiment, a composition according to the invention contains at least one non-volatile phenyl silicone oil as second non-volatile oil.

Representative examples of these non-volatile phenyl silicone oils that may be mentioned include:

the phenyl silicone oils corresponding to the following formula:

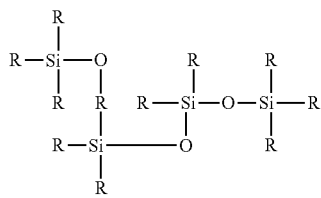

(I)

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

the phenyl silicone oils corresponding to the following formula:

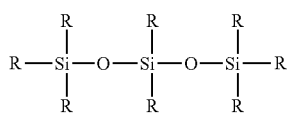

(II)

in which the groups R represent, independently of each other, a methyl or a phenyl, with the proviso that at least one group R represents a phenyl.

Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

the phenyl silicone oils corresponding to the following formula:

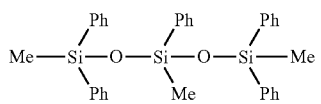

(III)

in which Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used.

the phenyl silicone oils corresponding to the following formula:

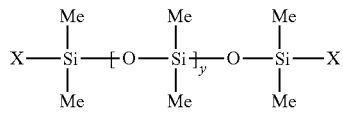 (IV)

in which Me represents methyl, y is between 1 and 1000 and X represents —$CH_2$—$CH(CH_3)(Ph)$.

the phenyl silicone oils corresponding to formula (V) below:

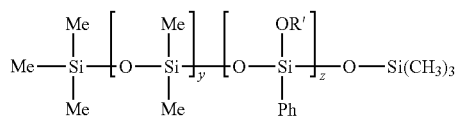 (V)

in which Me is methyl and Ph is phenyl, OR' represents a group —$OSiMe_3$ and y is 0 or ranges between 1 and 1000, and z ranges between 1 and 1000, such that compound (V) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid, the phenyl silicone oils corresponding to formula (VI) below, and mixtures thereof:

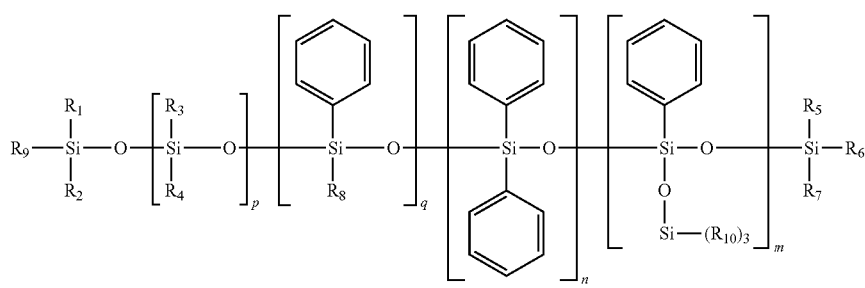 (VI)

in which:

$R_1$ to $R_{10}$, independently of each other, are saturated or unsaturated, linear, cyclic or branched $C_1$-$C_{30}$ hydrocarbon-based radicals, m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

the phenyl silicone oils corresponding to formula (VII) below, and mixtures thereof:

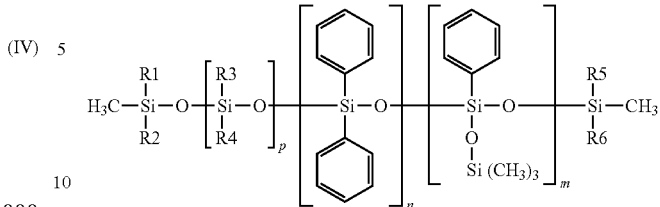 (VII)

in which:

$R_1$ to $R_6$, independently of each other, are saturated or unsaturated, linear, cyclic or branched $C_1$-$C_{30}$ hydrocarbon-based radicals, m, n and p are, independently of each other, integers between 0 and 100, with the proviso that the sum n+m is between 1 and 100.

Preferably, $R_1$ to $R_6$, independently of each other, represent a saturated, linear or branched $C_1$-$C_{30}$ and especially $C_1$-$C_{12}$ hydrocarbon-based radical and in particular a methyl, ethyl, propyl or butyl radical.

$R_1$ to $R_6$ may especially be identical, and in addition may be a methyl radical.

Preferably, m=1 or 2 or 3, and/or n=0 and/or p=0 or 1 may apply, in formula (VII).

the phenyl silicone oils corresponding to formula (VIII), and mixtures thereof:

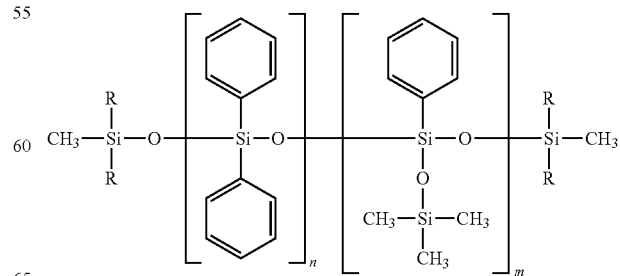 (VIII)

in which:
R is a $C_1$-$C_{30}$ alkyl radical, an aryl radical or an aralkyl radical,
n is an integer ranging from 0 to 100, and
m is an integer ranging from 0 to 100, with the proviso that the sum n+m ranges from 1 to 100.

In particular, the radicals R of formula (VIII) and $R_1$ to $R_{10}$ defined previously may each represent a linear or branched, saturated or unsaturated alkyl radical, especially of $C_2$-$C_{20}$, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical whose aryl and alkyl residues are as defined previously.

Preferably, R of formula (VIII) and $R_1$ to $R_{10}$ may each represent a methyl, ethyl, propyl, isopropyl, decyl, dodecyl or octadecyl radical, or alternatively a phenyl, tolyl, benzyl or phenethyl radical.

According to one embodiment, a phenyl silicone oil of formula (VIII) with a viscosity at 25° C. of between 5 and 1500 mm²/s (i.e. 5 to 1500 cSt), and preferably with a viscosity of between 5 and 1000 mm²/s (i.e. 5 to 1000 cSt) may be used.

As phenyl silicone oils of formula (VIII), it is especially possible to use phenyl trimethicones such as DC556 from Dow Corning (22.5 cSt), the oil Silbione 70663V30 from Rhône-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

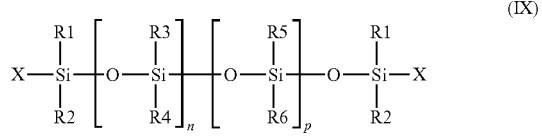

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms or an aryl radical,
X is an alkyl radical containing from 1 to 6 carbon atoms, a hydroxyl radical or a vinyl radical,
n and p being chosen so as to give the oil a weight-average molecular mass of less than 200 000 g/mol, preferably less than 150 000 g/mol and more preferably less than 100 000 g/mol.

The phenyl silicones are more particularly chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trim ethyl siloxysilicates, and mixtures thereof.

More particularly, the phenyl silicones are chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

As preferred non-volatile silicone oils, examples that may be mentioned include silicone oils such as:
phenyl silicones (also known as phenyl silicone oil) such as trimethylsiloxyphenyl dimethicone (for instance Belsil PDM 1000 from the company Wacker (MW=9000 g/mol) (cf. formula (V) above), phenyl trimethicones (such as the phenyl trimethicone sold under the trade name DC556 by Dow Corning), phenyl dimethicones, phenyltrimethyl siloxydiphenylsiloxanes, diphenyl dimethicones, diphenylmethyldiphenyltri siloxanes, 2-phenyl ethyl trimethyl siloxysilicates, trimethylpentaphenyl trisiloxane (such as the product sold under the name Dow Corning PH-1555 HRI Cosmetic fluid by Dow Corning) (cf. formula (III) above),
non-volatile polydimethylsiloxanes (PDMS), polydimethylsiloxanes comprising alkyl or alkoxy groups, which are pendent and/or at the end of the silicone chain, these groups each containing from 2 to 24 carbon atoms,
and mixtures thereof.

Preferably, the second non-volatile oil is a phenyl silicone oil.

Preferably, a phenyl silicone oil is used. According to one preferred embodiment, the phenyl silicone oil is chosen from trimethylsiloxyphenyl dimethicones.

According to one preferred embodiment, the non-volatile silicone oil(s) are present in a total content ranging from 5% to 75% by weight, in particular from 10% to 40% by weight and preferably from 15% to 30% by weight relative to the total weight of the said composition.

Non-Volatile Fluoro Oil

According to a second embodiment, the second non-volatile oil is a fluoro oil.

The term "fluoro oil" means an oil containing at least one fluorine atom.

The fluoro oils that may be used in the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to one particularly preferred embodiment, the fluoro oil according to the invention is chosen from perfluoro oils.

As examples of perfluoro oils that may be used in the invention, mention may be made of perfluorodecalins and perfluoroperhydrophenanthrenes.

According to one particularly preferred embodiment, the fluoro oil is chosen from perfluoroperhydrophenanthrenes, and especially the Fiflow® products sold by the company Créations Couleurs. In particular, use may be made of the fluoro oil whose INCI name is perfluoroperhydrophenanthrene, sold under the reference Fiflow 220 by the company F2 Chemicals.

According to a third embodiment, the said second non-volatile oil is a hydrocarbon-based oil, which is different from the said first oil.

According to a first embodiment, the second non-volatile hydrocarbon-based oil is chosen from apolar hydrocarbon-based oils.

For the purposes of the present invention, the term "apolar oil" means an oil whose solubility parameter at 25° C., $δ_a$, is equal to 0 $(J/cm^3)^{1/2}$.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

Preferably, the non-volatile apolar hydrocarbon-based oil is free of oxygen atoms.

Preferably, the non-volatile apolar hydrocarbon-based oil may be chosen from linear or branched hydrocarbons of mineral or synthetic origin, such as:

liquid paraffin or derivatives thereof, liquid petroleum jelly, naphthalene oil, polybutylenes such as Indopol H-100 (molar mass or MW=965 g/mol), Indopol H-300 (MW=1340 g/mol) and Indopol H-1500 (MW=2160 g/mol) sold or manufactured by the company Amoco, hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), decene/butene copolymers, polybutene/polyisobutene copolymers, especially Indopol L-14, polydecenes and hydrogenated polydecenes such as: Puresyn 10 (MW=723 g/mol) and Puresyn 150 (MW=9200 g/mol) sold or manufactured by the company Mobil Chemicals, and mixtures thereof.

According to a second embodiment, the second non-volatile hydrocarbon-based oil is chosen from polar hydrocarbon-based oils other than the said "first oil".

In particular, the said second polar non-volatile oil other than the said first oil may be an ester oil, in particular containing between 18 and 70 carbon atoms.

Examples that may be mentioned include monoesters, diesters or triesters.

The ester oils may especially be hydroxylated.

The non-volatile ester oil may preferably be chosen from:

monoesters comprising between 18 and 40 carbon atoms in total, in particular the monoesters of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 18$, for instance Purcellin oil (cetostearyl octanoate), isononyl isononanoate, $C_{12}$ to $C_{15}$ alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate. Preferably, they are esters of formula $R_1COOR_2$ in which $R_1$ represents a linear or branched fatty acid residue containing from 4 to 40 carbon atoms and $R_2$ represents a hydrocarbon-based chain that is especially branched, containing from 4 to 40 carbon atoms provided that $R_1+R_2 \geq 18$. Preferably, the ester comprises between 18 and 40 carbon atoms in total. Preferred monoesters that may be mentioned include isononyl isononanoate, oleyl erucate and/or 2-octyldodecyl neopentanoate;

diesters, especially comprising between 18 and 60 carbon atoms in total and in particular between 18 and 50 carbon atoms in total. It is especially possible to use diesters of dicarboxylic acids and of monoalcohols, preferably such as diisostearyl malate, or glycol diesters of monocarboxylic acids, such as neopentyl glycol diheptanoate or poly(2)glyceryl diisostearate (especially such as the compound sold under the trade reference Dermol DGDIS by the company Alzo);

triesters, especially comprising between 35 and 70 carbon atoms in total, in particular such as triesters of a tricarboxylic acid, such as triisostearyl citrate, or tridecyl trimellitate, or glycol triesters of monocarboxylic acids such as poly(2)glyceryl triisostearate;

tetraesters, especially with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, poly(2)glyceryl tetraisostearate or pentaerythrityl tetrakis(2-decyl)tetradecanoate;

polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or copolymers of polyols and of diacid dimers, and esters thereof, such as Hailuscent ISDA;

esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid especially of $C_8$ to $C_{24}$, especially of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;

vinylpyrrolidone/1-hexadecene copolymers, for instance the product sold under the name Antaron V-216 (also known as Ganex V216) by the company ISP (MW=7300 g/mol), hydrocarbon-based plant oils such as fatty acid triglycerides (which are liquid at room temperature), especially of fatty acids containing from 7 to 40 carbon atoms, such as heptanoic or octanoic acid triglycerides or jojoba oil; mention may be made in particular of saturated triglycerides such as caprylic/capric triglycerides, glyceryl triheptanoate, glyceryl trioctanoate, and $C_{18-36}$ acid triglycerides such as those sold under the reference Dub TGI 24 sold by Stéarineries Dubois, and unsaturated triglycerides such as castor oil, olive oil, ximenia oil and pracaxi oil;
and mixtures thereof.

Additional Oils

The composition according to the invention may comprise, besides the non-volatile hydrocarbon-based "first oil" and besides the non-volatile "second oil" chosen from silicone oils and/or fluoro oils or hydrocarbon-based oils other than the said first oil, at least one additional oil other than these oils.

In particular, the additional oil may be chosen from volatile oils, in particular volatile hydrocarbon-based oils, volatile silicone oils and/or volatile fluoro oils.

The additional volatile oil may especially be a silicone oil, a hydrocarbon-based oil, which is preferably apolar, or a fluoro oil.

According to a first embodiment, the additional volatile oil is a silicone oil and may be chosen especially from silicone oils with a flash point ranging from 40° C. to 102° C., preferably with a flash point of greater than 55° C. and less than or equal to 95° C., and preferentially ranging from 65° C. to 95° C.

As additional volatile silicone oils that may be used in the invention, mention may be made of linear or cyclic silicones with a viscosity at room temperature of less than 8 centistokes (cSt) ($8 \times 10^{-6}$ $m^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to a second embodiment, the additional volatile oil is a fluoro oil, such as nonafluoromethoxybutane or perfluoromethylcyclopentane, and mixtures thereof.

According to a third embodiment, the additional volatile oil is a hydrocarbon-based oil, which is preferably apolar.

The additional apolar volatile hydrocarbon-based oil may have a flash point ranging from 40° C. to 102° C., preferably ranging from 40° C. to 55° C. and preferentially ranging from 40° C. to 50° C.

The additional hydrocarbon-based volatile oil may especially be chosen from hydrocarbon-based volatile oils containing from 8 to 16 carbon atoms, and mixtures thereof, and especially:
branched $C_8$-$C_{16}$ alkanes such as $C_8$-$C_{16}$ isoalkanes (also known as isoparaffins), isododecane, isodecane and isohexadecane, and, for example, the oils sold under the trade name Isopar or Permethyl,
linear alkanes, for example such as n-dodecane (C12) and n-tetradecane (C14) sold by Sasol under the references, respectively, Parafol 12-97 and Parafol 14-97, and also mixtures thereof, the undecane-tridecane mixture (Cetiol UT), mixtures of n-undecane (C11) and of n-tridecane (C13) obtained in Examples 1 and 2 of patent application WO 2008/155 059 from the company Cognis, and mixtures thereof.

According to one particular embodiment, the additional volatile oil(s) may be present in a content ranging from 0.1% to 30% by weight and especially from 0.5% to 20% by weight relative to the total weight of the said composition.

Advantageously, the composition contains less than 10% by weight of monoalcohols containing from 1 to 5 carbon atoms, and preferably less than 5%.

According to one particular embodiment, the composition may be free of monoalcohols containing from 1 to 5 carbon atoms.

According to a preferred embodiment, the composition is free of additional volatile oil.

In a preferred embodiment, the composition comprises from 4 to 30% by weight of alkylcellulose, preferably of ethylcellulose, from 15 to 50% by weight of water, and from 45 to 75% by weight of non volatile oils.

Other Fatty Substances

Besides the oil described previously, the composition under consideration according to the invention may also comprise at least one solid fatty substance chosen from waxes and/or pasty fatty substances, and mixtures thereof.

Wax(es)

The composition according to the invention may comprise at least one wax.

For the purposes of the invention, the term "wax" means a lipophilic compound, which is solid at room temperature (25° C.), with a reversible solid/liquid change of state, which has a melting point of greater than or equal to 30° C., which may be up to 120° C.

The waxes that may be used in a composition according to the invention are chosen from solid waxes that may or may not be deformable at room temperature of animal, plant, mineral or synthetic origin, and mixtures thereof.

Hydrocarbon-based waxes, for instance beeswax, lanolin wax or Chinese insect wax; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may especially be mentioned are hydrogenated jojoba oil, hydrogenated sunflower oil, hydrogenated castor oil, hydrogenated coconut oil, hydrogenated lanolin oil, bis(1,1,1-trimethylolpropane) tetrastearate sold under the name Hest 2T-4S by the company Heterene, and bis(1,1,1-trimethylolpropane) tetrabehenate sold under the name Hest 2T-4B by the company Heterene.

The waxes obtained by transesterification and hydrogenation of plant oils, such as castor oil or olive oil, for instance the waxes sold under the names Phytowax ricin 16L64® and 22L73® and Phytowax Olive 18L57 by the company Sophim, may also be used. Such waxes are described in patent application FR-A-2 792 190.

It is also possible to use silicone waxes, which may advantageously be substituted polysiloxanes, preferably of low melting point.

Among the commercial silicone waxes of this type, mention may be made especially of those sold under the names Abilwax 9800, 9801 or 9810 (Goldschmidt), KF910 and KF7002 (Shin-Etsu), or 176-1118-3 and 176-11481 (General Electric).

The silicone waxes that may be used may also be alkyl or alkoxy dimethicones such as the following commercial products: Abilwax 2428, 2434 and 2440 (Goldschmidt), or VP 1622 and VP 1621 (Wacker), and also ($C_{20}$-$C_{60}$) alkyl dimethicones, in particular ($C_{30}$-$C_{45}$) alkyl dimethicones, such as the silicone wax sold under the name SF-1642 by the company GE-Bayer Silicones.

It is also possible to use hydrocarbon-based waxes modified with silicone or fluoro groups, for instance: siliconyl candelilla, siliconyl beeswax and fluoro beeswax from Koster Keunen.

The waxes may also be chosen from fluoro waxes.

According to one embodiment, the composition according to the invention is free of wax.

Pasty Fatty Substances

The composition under consideration according to the invention may also comprise at least one pasty fatty substance.

For the purposes of the present invention, the term "pasty fatty substance" (also known as a paste) means a lipophilic fatty compound with a reversible solid/liquid change of state, displaying anisotropic crystal organization in the solid state, and comprising a liquid fraction and a solid fraction at a temperature of 23° C.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

For the purposes of the invention, the melting point corresponds to the temperature of the most endothermic peak observed on thermal analysis (DSC) as described in standard ISO 11357-3; 1999. The melting point of a pasty substance or of a wax may be measured using a differential scanning calorimeter (DSC), for example the calorimeter sold under the name MDSC 2920 by the company TA Instruments.

The measuring protocol is as follows:

A sample of 5 mg of paste or wax (depending on the case) placed in a crucible is subjected to a first temperature rise passing from −20° C. to 100° C., at the heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference between the power absorbed by the empty crucible and the crucible containing the sample of paste or wax as a function of the temperature is measured. The melting point of the compound is the temperature value corresponding to the top of the peak of the curve representing the variation in the difference in power absorbed as a function of the temperature.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., constituted of a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty fatty compound may preferably be chosen from synthetic compounds and compounds of plant origin. A pasty fatty substance may be obtained by synthesis from starting materials of plant origin.

The pasty fatty substance is advantageously chosen from:
lanolin and derivatives thereof, such as lanolin alcohol, oxyethylenated lanolins, acetylated lanolin, lanolin esters such as isopropyl lanolate, and oxypropylenated lanolins,
polymeric or non-polymeric silicone compounds, for instance polydimethylsiloxanes of high molecular masses, polydimethylsiloxanes containing side chains of the alkyl or alkoxy type containing from 8 to 24 carbon atoms, especially stearyl dimethicones,
polymeric or non-polymeric fluoro compounds,
vinyl polymers, especially:
olefin homopolymers,
olefin copolymers,
hydrogenated diene homopolymers and copolymers,
linear or branched oligomers, homopolymers or copolymers of alkyl (meth)acrylates preferably containing a $C_8$-$C_{30}$ alkyl group,
oligomers, homopolymers and copolymers of vinyl esters containing $C_8$-$C_{30}$ alkyl groups,
oligomers, homopolymers and copolymers of vinyl ethers containing $C_8$-$C_{30}$ alkyl groups,
liposoluble polyethers resulting from the polyetherification between one or more $C_2$-$C_{100}$ and preferably $C_2$-$C_{50}$ diols,
esters and polyesters,
and mixtures thereof.

The pasty fatty substance may be a polymer, especially a hydrocarbon-based polymer.

A preferred silicone and fluoro pasty fatty substance is polymethyltrifluoropropylmethylalkyldimethylsiloxane, sold under the name X22-1088 by Shin-Etsu.

When the pasty fatty substance is a silicone and/or fluoro polymer, the composition advantageously comprises a compatibilizer such as short-chain esters, for instance isodecyl neopentanoate.

Among the liposoluble polyethers, mention may be made especially of copolymers of ethylene oxide and/or of propylene oxide with $C_6$-$C_{30}$ alkylene oxides. Preferably, the weight ratio of the ethylene oxide and/or propylene oxide to the alkylene oxides in the copolymer is from 5/95 to 70/30. In this family, mention will be made especially of block copolymers comprising $C_6$-$C_{30}$ alkylene oxide blocks with a molecular weight ranging from 1000 to 10 000, for example a polyoxyethylene/polydodecylene glycol block copolymer such as the ethers of dodecanediol (22 mol) and of polyethylene glycol (45 oxyethylene or OE units) sold under the brand name Elfacos ST9 by Akzo Nobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol;
phytosterol esters;
pentaerythritol esters;
esters formed from:
at least one $C_{16-40}$ alcohol, at least one of the alcohols being a Guerbet alcohol, and
a diacid dimer formed from at least one unsaturated $C_{18-40}$ fatty acid,
such as the ester of a dimer of fatty acids and of tall oil comprising 36 carbon atoms and of a mixture i) of Guerbet alcohols comprising 32 carbon atoms and ii) of behenyl alcohol; the ester of a dimer of linoleic acid and of a mixture of two Guerbet alcohols, 2-tetradecyloctadecanol (32 carbon atoms) and 2-hexadecyleicosanol (36 carbon atoms);
non-crosslinked polyesters resulting from the polycondensation between a linear or branched $C_4$-$C_{50}$ dicarboxylic acid or polycarboxylic acid and a $C_2$-$C_{50}$ diol or polyol,
polyesters resulting from the esterification between a polycarboxylic acid and an aliphatic hydroxylated carboxylic acid, such as Risocast DA-L and Risocast DA-H sold by the Japanese company Kokyu Alcohol Kogyo, which are esters resulting from the esterification reaction of hydrogenated castor oil with dilinoleic acid or isostearic acid; and
aliphatic esters of an ester resulting from the esterification between an ester of an aliphatic hydroxycarboxylic acid and an aliphatic carboxylic acid, for example the product sold under the trade name Salacos HClS (V)-L by the company Nisshin Oil.

A Guerbet alcohol is the reaction product of the Guerbet reaction, which is well known to those skilled in the art. It is a reaction for transforming a primary aliphatic alcohol into its β-alkyl dimeric alcohol with loss of one equivalent of water.

The aliphatic carboxylic acids described above generally comprise from 4 to 30 and preferably from 8 to 30 carbon atoms. They are preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof.

The aliphatic carboxylic acids are preferably branched.

The aliphatic hydroxycarboxylic acid esters are advantageously derived from an aliphatic hydroxycarboxylic acid comprising from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid esters are especially chosen from:
a) partial or total esters of saturated linear monohydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated polyhydroxylated aliphatic polycarboxylic acids;
e) partial or total esters of $C_2$ to $C_{16}$ aliphatic polyols that have reacted with a monohydroxylated or polyhydroxylated aliphatic monocarboxylic or polycarboxylic acid,
f) and mixtures thereof.

The aliphatic esters of an ester are advantageously chosen from:
the ester resulting from the esterification reaction of hydrogenated castor oil with isostearic acid in proportions of 1 to 1 (1/1), known as hydrogenated castor oil monoisostearate,
the ester resulting from the esterification reaction of hydrogenated castor oil with isostearic acid in proportions of 1 to 2 (1/2), known as hydrogenated castor oil diisostearate,
the ester resulting from the esterification reaction of hydrogenated castor oil with isostearic acid in proportions of 1 to 3 (1/3), known as hydrogenated castor oil triisostearate,
and mixtures thereof.

The pasty fatty substance(s) may be present in an amount ranging from 0.5% to 30% by weight and especially from 1% to 20% by weight relative to the total weight of the composition.

A composition used according to the invention may comprise, besides the abovementioned compounds, at least one structuring agent chosen from semi-crystalline polymers, and mixtures thereof.

Semi-Crystalline Polymer

The composition according to the invention may also comprise at least one semi-crystalline polymer, in particular a semi-crystalline polymer of organic structure whose melting point is greater than or equal to 30° C.

Preferably, the total amount of semi-crystalline polymer(s) represents from 2% to 20% by weight, for example from 3% to 15% by weight and better still from 4% to 10% by weight relative to the total weight of the composition.

For the purposes of the invention, the term "polymers" means compounds comprising at least two repeating units, preferably at least three repeating units and more especially at least ten repeating units.

For the purposes of the invention, the term "semi-crystalline polymer" means polymers comprising a crystallizable portion and an amorphous portion in the backbone and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The terms "organic compound" and "having an organic structure" mean compounds containing carbon atoms and hydrogen atoms and optionally heteroatoms such as S, O, N or P, alone or in combination.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is preferably greater than or equal to 30° C. and less than 70° C.

The semi-crystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5° C. or 10° C. per minute. (The melting point under consideration is the point corresponding to the temperature of the most endothermic peak of the thermogram).

The semi-crystalline polymer(s) according to the invention preferably have a melting point that is higher than the temperature of the keratinous support intended to receive the said composition, in particular the skin or the lips.

According to the invention, the semi-crystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which are pendent or lateral relative to the polymer backbone. A "block" is a group of atoms belonging to the backbone, this group constituting one of the repeating units of the polymer.

According to one preferred embodiment, the semi-crystalline polymer is chosen from:
homopolymers and copolymers comprising units resulting from the polymerization of one or more monomers bearing crystallizable hydrophobic side chain(s),
polymers bearing in the backbone at least one crystallizable block,
polycondensates of aliphatic or aromatic or aliphatic/aromatic polyester type copolymers of ethylene and propylene prepared via metallocene catalysis.

The semi-crystalline polymers that may be used in the invention may in particular be chosen from:
block copolymers of polyolefins of controlled crystallization, whose monomers are described in EP-A-0 951 897,
polycondensates, especially of aliphatic or aromatic of aliphatic/aromatic polyester type,
copolymers of ethylene and propylene prepared via metallocene catalysis,
homopolymers or copolymers bearing at least one crystallizable side chain and homopolymers or copolymers bearing at least one crystallizable block in the backbone, for instance those described in document U.S. Pat. No. 5,156,911,
homopolymers or copolymers bearing at least one crystallizable side chain, in particular bearing fluoro group(s), such as those described in document WO-A-01/19333,
and mixtures thereof.

Examples of semi-crystalline polymers that may be mentioned include those described in patent application WO 2010/010 301, the content of which is incorporated by reference.

Aqueous Phase

As stated hereinabove, a composition according to the invention comprises water.

Preferably, the composition according to the invention comprises at least 2% by weight of water, preferably at least 5% by weight and preferably at least 10% by weight, relative to the total weight of the composition.

The water may be present in a total content ranging from 2% to 80% by weight. Preferably, the water is present in a total content ranging from 15% to 50% by weight, relative to the total weight of the composition.

The composition in accordance with the invention may comprise, besides water, at least one water-soluble solvent.

The aqueous phase may constitute the continuous phase of the composition.

The term "composition with an aqueous continuous phase" means that the composition has a conductivity, measured at 25° C., of greater than or equal to 23 µS/cm (microSiemens/cm), the conductivity being measured, for example, using an MPC227 conductimeter from Mettler Toledo and an Inlab730 conductivity measuring cell. The measuring cell is immersed in the composition so as to remove the air bubbles that might be formed between the two electrodes of the cell. The conductivity reading is taken once the conductimeter value has stabilized. A mean is determined on at least three successive measurements.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the compositions according to the invention may also be volatile.

Among the water-soluble solvents that may be used in the compositions in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$-$C_4$ ketones and $C_2$-$C_4$ aldehydes.

The aqueous phase (water and optionally the water-miscible solvent) may be present in the composition in a content ranging from 2% to 95% by weight and preferably ranging from 5% to 80% by weight relative to the total weight of the composition. In a particularly preferred manner, the aqueous phase (water and optionally the water-miscible solvent) is present in the composition in a content ranging from 10% to 60% by weight, preferably from 15% to 50% by weight and preferably from 20% to 40% by weight relative to the total weight of the composition.

The aqueous phase according to the invention may also comprise at least one hydrophilic film-forming polymer and/or at least one hydrophilic thickener and/or at least one surfactant. However, the content of aqueous phase indicated previously does not include the contents of each of the abovementioned compounds.

According to one particularly preferred embodiment, the composition according to the invention is an oil-in-water emulsion.

Stabilizer:

The composition according to the invention comprises at least one stabilizer chosen from surfactants and/or hydrophilic gelling agents, preferably chosen from associative polymers, natural polymers and their mixture.

Preferably, the composition is such that the surfactant, if present, is in a content ranging from 0.1% to 20% by weight, relative to the total weight of the composition.

Preferably, the composition is such that the hydrophilic gelling agent (preferably an associative polymer), if present, is in a content ranging from 0.1% to 10% by weight, relative to the total weight of the composition.

Surfactants

The composition according to the invention may contain an emulsifying system comprising one or more surfactants that are especially present in a content ranging from 0.1% to 20% by weight, or even 0.5% to 15% by weight and preferably ranging from 1% to 10% by weight relative to the total weight of the composition.

Advantageously, when the composition comprises a surfactant, this surfactant is present in a content such that the total content of non-volatile oils/content of surfactant(s) weight ratio is between 1 and 40 and preferably between 5 and 35.

Preferably, they are present in a total content of non-volatile oils/content of surfactant(s) weight ratio of between 8 and 25.

An emulsifying surfactant appropriately chosen to obtain an oil-in-water emulsion is preferably used.

In particular, an emulsifying surfactant having at 25° C. an HLB balance (hydrophilic-lipophilic balance) within the Griffin sense of greater than or equal to 8 may be used.

An emulsifying surfactant having at 25° C. an HLB balance (hydrophilic-lipophilic balance) within the Griffin sense of less than 8 may also be used.

The Griffin HLB value is defined in J. Soc. Cosm. Chem. 1954 (volume 5), pages 249-256.

These surfactants may be chosen from nonionic, anionic, cationic and amphoteric surfactants, and mixtures thereof. Reference may be made to Kirk-Othmer's *Encyclopedia of Chemical Technology*, Volume 22, pp. 333-432, 3rd Edition, 1979, Wiley, for the definition of the emulsifying properties and functions of surfactants, in particular pp. 347-377 of this reference, for the anionic, amphoteric and nonionic surfactants.

According to a first embodiment, the composition comprises at least one hydrocarbon-based surfactant.

Examples of hydrocarbon-based surfactants that are suitable for use in the invention are described below.

According to one particularly preferred embodiment, as seen previously, the composition of the invention comprises at least one surfactant chosen from anionic and nonionic surfactants, which is introduced, at least partly, via the aqueous dispersion of alkylcellulose used during the preparation of a composition of the invention.

Nonionic Surfactants

The nonionic surfactants may especially be chosen from alkyl and polyalkyl esters of poly(ethylene oxide), oxyalkylenated alcohols, alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, and optionally polyoxyethylenated alkyl and polyalkyl ethers of glycerol, and mixtures thereof.

1) Alkyl and polyalkyl esters of poly(ethylene oxide) that are preferably used include those with a number of ethylene oxide (EO) units ranging from 2 to 200. Examples that may be mentioned include stearate 40 EO, stearate 50 EO, stearate 100 EO, laurate 20 EO, laurate 40 EO and distearate 150 EO.

2) Alkyl and polyalkyl ethers of poly(ethylene oxide) that are preferably used include those with a number of ethylene oxide (EO) units ranging from 2 to 200. Examples that may be mentioned include cetyl ether 23 EO, oleyl ether 50 EO, phytosterol 30 EO, steareth 40, steareth 100 and beheneth 100.

3) As oxyalkylenated alcohols, which are in particular oxyethylenated and/or oxypropylenated, use is preferably made of those that can comprise from 1 to 150 oxyethylene and/or oxypropylene units, in particular containing from 20 to 100 oxyethylene units, in particular ethoxylated fatty alcohols, especially of $C_8$-$C_{24}$ and preferably of $C_{12}$-$C_{18}$, such as stearyl alcohol ethoxylated with 20 oxyethylene units (CTFA name Steareth-20), for instance Brij 78 sold by the company Uniqema, cetearyl alcohol ethoxylated with 30 oxyethylene units (CTFA name Ceteareth-30), and the mixture of $C_{12}$-$C_{15}$ fatty alcohols comprising 7 oxyethylene units (CTFA name $C_{12}$-$C_{15}$ Pareth-7), for instance the product sold under the name Neodol 25-7® by Shell Chemicals; or in particular oxyalkylenated (oxyethylenated and/or oxypropylenated) alcohols containing from 1 to 15 oxyethylene and/or oxypropylene units, in particular ethoxylated $C_8$-$C_{24}$ and preferably $C_{12}$-$C_{18}$ fatty alcohols, such as stearyl alcohol ethoxylated with 2 oxyethylene units (CTFA name Steareth-2), for instance Brij 72 sold by the company Uniqema;

4) Optionally polyoxyethylenated alkyl and polyalkyl esters of sorbitan that are preferably used include those with a number of ethylene oxide (EO) units ranging from 0 to 100. Examples that may be mentioned include sorbitan laurate 4 or 20 EO, in particular polysorbate 20 (or polyoxyethylene (20) sorbitan monolaurate) such as the product Tween 20 sold by the company Uniqema, sorbitan palmitate 20 EO, sorbitan stearate 20 EO, sorbitan oleate 20 EO, or the Cremophor products (RH 40, RH 60, etc.) from BASF.

5) Optionally polyoxyethylenated alkyl and polyalkyl ethers of sorbitan that are preferably used include those with a number of ethylene oxide (EO) units ranging from 0 to 100.

6) Alkyl and polyalkyl glucosides or polyglucosides that are preferably used include those containing an alkyl group comprising from 6 to 30 carbon atoms and preferably from 6 to 18 or even from 8 to 16 carbon atoms, and containing a glucoside group preferably comprising from 1 to 5 and especially 1, 2 or 3 glucoside units. The alkylpolyglucosides may be chosen, for example, from decylglucoside (alkyl-$C_9$/$C_{11}$-polyglucoside (1.4)), for instance the product sold under the name Mydol 10® by the company Kao Chemicals or the product sold under the name Plantacare 2000 UP® by the company Henkel and the product sold under the name Oramix NS 10® by the company SEPPIC; caprylyl/capryl glucoside, for instance the product sold under the name Plantacare KE 3711® by the company Cognis or Oramix CG 110® by the company SEPPIC; laurylglucoside, for instance the product sold under the name Plantacare 1200 UP® by the company Henkel or Plantaren 1200 N® by the company Henkel; cocoglucoside, for instance the product sold under the name Plantacare 818 UP® by the company Henkel; caprylylglucoside, for instance the product sold under the name Plantacare 810 UP® by the company Cognis; and mixtures thereof.

More generally, the surfactants of alkylpolyglycoside type are defined more specifically hereinbelow.

7) Examples of alkyl and polyalkyl esters of sucrose that may be mentioned include Crodesta F150, sucrose monolaurate sold under the name Crodesta SL 40, and the products sold by Ryoto Sugar Ester, for instance sucrose palmitate sold under the reference Ryoto Sugar Ester P1670, Ryoto Sugar Ester LWA1695 or Ryoto Sugar Ester 01570.

8) Optionally polyoxyethylenated alkyl and polyalkyl esters of glycerol that are preferably used include those with a number of ethylene oxide (EO) units ranging from 0 to 100 and a number of glycerol units ranging from 1 to 30. Examples that may be mentioned include hexaglyceryl monolaurate and PEG-30 glyceryl stearate.

9) Optionally polyoxyethylenated alkyl and polyalkyl ethers of glycerol that are preferably used include those with a number of ethylene oxide (EO) units ranging from 0 to 100 and a number of glycerol units ranging from 1 to 30. Examples that may be mentioned include Nikkol batyl alcohol 100 and Nikkol chimyl alcohol 100.

Anionic Surfactants

The anionic surfactants may be chosen from alkyl ether sulphates, carboxylates, amino acid derivatives, sulphonates, isethionates, taurates, sulphosuccinates, alkylsulphoacetates, phosphates and alkyl phosphates, polypeptides, metal salts of $C_{10}$-$C_{30}$ and especially $C_{12}$-$C_{20}$ fatty acids, in particular metal stearates, and mixtures thereof.

1) Examples of alkyl ether sulphates that may be mentioned include sodium lauryl ether sulphate (70/30 C12-14) (2.2 EO) sold under the names Sipon AOS225 or Texapon N702 by the company Henkel, ammonium lauryl ether sulphate (70/30 C12-14) (3 EO) sold under the name Sipon LEA 370 by the company Henkel, ammonium ($C_{12}$-$C_{14}$) alkyl ether (9 EO) sulfate sold under the name Rhodapex AB/20 by the company Rhodia Chimie, and the mixture of sodium magnesium lauryl oleyl ether sulfate sold under the name Empicol BSD 52 by the company Albright & Wilson.

2) Examples of carboxylates that may be mentioned include salts (for example alkali metal salts) of N-acylamino acids, glycol carboxylates, amido ether carboxylates (AEC) and polyoxyethylenated carboxylic acid salts.

The surfactant of glycol carboxylate type may be chosen from alkyl glycol carboxylics or 2-(2-hydroxyalkyloxy acetate), salts thereof and mixtures thereof. These alkyl glycol carboxylics comprise a linear or branched, saturated or unsaturated, aliphatic and/or aromatic alkyl chain containing from 8 to 18 carbon atoms. These carboxylics may be neutralized with mineral bases such as potassium hydroxide or sodium hydroxide.

Examples of surfactants of glycol carboxylic type that may be mentioned include sodium lauryl glycol carboxylate or sodium 2-(2-hydroxyalkyloxy acetate) such as the product sold under the name Beaulight Shag by the company Sanyo, Beaulight LCA-25N® or the corresponding acid form Beaulight Shaa (Acid form)®.

An example of an amido ether carboxylate (AEC) that may be mentioned include sodium lauryl amido ether carboxylate (3 EO) sold under the name Akypo Foam 30® by the company Kao Chemicals.

Examples of polyoxyethylenated carboxylic acid salts that may be mentioned include oxyethylenated (6 EO) sodium lauryl ether carboxylate (65/25/10 $C_{12\text{-}14\text{-}16}$) sold under the name Akypo Soft 45 NV® by the company Kao Chemicals, polyoxyethylenated and carboxymethylated fatty acids of olive oil origin sold under the name Olivem 400® by the company Biologia e Tecnologia, and oxyethylenated (6 EO) sodium tridecyl ether carboxylate sold under the name Nikkol ECTD-6 NEX® by the company Nikkol.

3) Amino acid derivatives that may especially be mentioned include alkali metal salts of amino acids, such as:

sarcosinates, for instance the sodium lauroyl sarcosinate sold under the name Sarkosyl NL 97® by the company Ciba or sold under the name Oramix L30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol;

alaninates, for instance sodium N-lauroyl N-methyl amidopropionate sold under the name Sodium Nikkol Alaninate LN30® by the company Nikkol, or sold under the name Alanone ALE® by the company Kawaken, and triethanolamine N-lauroyl N-methyl alanine sold under the name Alanone Alta® by the company Kawaken;

glutamates, for instance triethanolamine monococoyl glutamate sold under the name Acylglutamate CT-12® by the company Ajinomoto, or triethanolamine lauroyl glutamate sold under the name Acylglutamate LT-12® by the company Ajinomoto.

The glutamic acid salts and/or derivatives are described more specifically hereinbelow.

aspartates, for instance the mixture of triethanolamine N-lauroyl aspartate and of triethanolamine N-myristoyl aspartate, sold under the name Asparack® by the company Mitsubishi;

glycine derivatives (glycinates), for instance the sodium N-cocoyl glycinate sold under the names Amilite GCS-12® and Amilite GCK 12 by the company Ajinomoto;

citrates, such as the oxyethylenated (9 mol) citric monoester of cocoyl alcohols sold under the name Witconol EC 1129 by the company Goldschmidt;

galacturonates, such as the sodium dodecyl-D-galactoside uronate sold by the company Soliance.

4) Examples of sulfonates that may be mentioned include α-olefin sulfonates, for instance the sodium α-olefin sulfonate ($C_{14\text{-}16}$) sold under the name Bio-Terge AS 40® by the company Stepan, sold under the names Witconate AOS Protégé® and Sulframine AOS PH 12® by the company Witco or sold under the name Bio-Terge AS 40 CG® by the company Stepan, the sodium secondary olefin sulfonate sold under the name Hostapur SAS 30® by the company Clariant.

5) Isethionates that may be mentioned include acylisethionates, for instance sodium cocoylisethionate, such as the product sold under the name Jordapon CI P® by the company Jordan.

6) Taurates that may be mentioned include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

7) Examples of sulfosuccinates that may be mentioned include the oxyethylenated (3 EO) lauryl alcohol monosulfosuccinate (70/30 $C_{12}/C_{14}$) sold under the names Setacin 103 Special® and Rewopol SB-FA 30 K 4® by the company Witco, the disodium salt of a $C_{12}$-$C_{14}$ alkyl hemisulfosuccinate, sold under the name Setacin F Special Paste® by the company Zschimmer Schwarz, the oxyethylenated (2 EO) disodium oleamidosulfosuccinate sold under the name Standapol SH 135® by the company Henkel, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco. Polydimethylsiloxane sulfosuccinates may also be used, such as disodium PEG-12 dimethicone sulfosuccinate sold under the name Mackanate-DC30 by the company MacIntyre.

8) Examples of alkyl sulfoacetates that may be mentioned include the mixture of sodium lauryl sulfoacetate and disodium lauryl ether sulfosuccinate, sold under the name Stepan Mild LSB by the company Stepan.

9) Examples of phosphates and alkyl phosphates that may be mentioned include monoalkyl phosphates and dialkyl phosphates, such as the lauryl monophosphate sold under the name MAP 20® by the company Kao Chemicals, the potassium salt of dodecylphosphoric acid, mixture of monoester and diester (predominantly diester) sold under the name Crafol AP-31® by the company Cognis, the mixture of octylphosphoric acid monoester and diester sold under the name Crafol AP-20® by the company Cognis, the mixture of ethoxylated (7 mol of EO) phosphoric acid diester of 2-butyloctanol, sold under the name Isofol 12 7 EO-Phosphate Ester® by the company Condea, the potassium or triethanolamine salt of mono($C_{12}$-$C_{13}$)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

10) The polypeptides are obtained, for example, by condensation of a fatty chain onto amino acids from cereals and especially from wheat and oat. Examples of polypeptides that may be mentioned include the potassium salt of hydrolysed lauroyl wheat protein, sold under the name Aminofoam W OR by the company Croda, the triethanolamine salt of hydrolysed cocoyl soybean protein, sold under the name May-Tein SY by the company Maybrook, the sodium salt of lauroyl oat amino acids, sold under the name Proteol Oat by the company SEPPIC, collagen hydrolysate grafted onto coconut fatty acid, sold under the name Geliderm 3000 by the company Deutsche Gelatine, and soybean proteins acylated with hydrogenated coconut acids, sold under the name Proteol VS 22 by the company SEPPIC.

11) As metal salts of $C_{10}$-$C_{30}$ and especially $C_{12}$-$C_{20}$ fatty acids, mention may be made in particular of metal stearates, such as sodium stearate and potassium stearate, and also polyhydroxystearates.

Cationic Surfactants

The cationic surfactants may be chosen from:
alkylimidazolidiniums such as isostearylethylimidonium ethosulfate,
ammonium salts such as ($C_{12\text{-}30}$ alkyl)tri($C_{1\text{-}4}$ alkyl)ammonium halides, for instance N,N,N-trimethyl-1-docosanaminium chloride (or behentrimonium chloride);

The compositions according to the invention may also contain one or more amphoteric surfactants, for instance N-acylamino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

According to a second embodiment, the composition comprises at least one silicone surfactant. Examples that may be mentioned include:

a) nonionic surfactants with an HLB of greater than or equal to 8 at 25° C., used alone or as a mixture; mention may be made especially of:
dimethicone copolyol, such as the product sold under the name Q2-5220® by the company Dow Corning;
dimethicone copolyol benzoate, such as the product sold under the names Finsolv SLB 101® and 201® by the company Finetex;

b) nonionic surfactants with an HLB of greater than or equal to 8 at 25° C., used alone or as a mixture; mention may be made especially of:
the mixture of cyclomethicone/dimethicone copolyol sold under the name Q2-3225C® by the company Dow Corning.

Hydrophilic Gelling Polymers

For the purposes of the present patent application, the term "polymer for gelling the aqueous phase" means a polymer that is capable of gelling the aqueous phase of the compositions according to the invention.

The gelling polymer that may be used according to the invention may especially be characterized by its capacity to form in water, beyond a certain concentration C*, a gel characterized by oscillatory rheology (μ=1 Hz) by a flow threshold $\tau_c$ at least equal to 10 Pa. This concentration C* may vary widely according to the nature of the gelling polymer under consideration.

By way of illustration, this concentration is between 1% and 2% by weight for an acrylamide/sodium acrylamido-2-methylpropanesulfonate copolymer as an inverse emulsion at 40% in polysorbate 80/1-C16, for instance the product sold under the name Simulgel 600 by the company SEPPIC, and is about 0.5% by weight for an AMPS/ethoxylated (25 EO) cetearyl methacrylate copolymer crosslinked with trimethylolpropane triacrylate (TMPTA) of the type such as Aristoflex HMS.

The gelling polymer may be present in the composition in an amount that is sufficient to adjust the stiffness modulus G* (1 Hz, 25° C.) of the composition to a value greater than or equal to 10 000 Pa and especially ranging from 10 000 Pa to 100 000 Pa. The method for measuring the stiffness modulus G* (1 Hz, 25° C.) of the composition is described in greater detail hereinbelow.

The gelling polymer is a hydrophilic polymer and is thus present in the aqueous phase of the composition.

More particularly, this gelling polymer may be chosen from:
acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglycerides) sold under the name Luvigel EM by the company, copolymers of acrylic acid and of acrylamide sold in the form of the sodium salt thereof under the names Reten by the company Hercules, the sodium polymethacrylate sold under the name Darvan No. 7 by the company Vanderbilt, and the sodium salts of polyhydroxycarboxylic acids sold under the name Hydagen F by the company Henkel, polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol EDT 2020, and even more preferentially Pemulen TR-2;

AMPS (polyacrylamidomethylpropanesulfonic acid partially neutralized with aqueous ammonia and highly crosslinked) sold by the company Clariant, AMPS/acrylamide copolymers of Sepigel or Simulgel type sold by the company SEPPIC, and polyoxyethylenated AMPS/alkyl methacrylate copolymers (crosslinked or non-crosslinked) of the type such as Aristoflex HMS sold by the company Clariant, and mixtures thereof.

Other examples of hydrophilic gelling polymers that may be mentioned include:

anionic, cationic, amphoteric or nonionic chitin or chitosan polymers;

cellulose polymers, other than alkylcellulose, chosen from hydroxyethylcellulose, hydroxypropylcellulose, hydroxymethylcellulose, ethylhydroxyethylcellulose and carboxymethylcellulose, and also quaternized cellulose derivatives;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

optionally modified polymers of natural origin, such as: galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;

alginates and carrageenans;

glycoaminoglycans, hyaluronic acid and derivatives thereof;

deoxyribonucleic acid;

mucopolysaccharides such as hyaluronic acid and chondroitin sulfates, and mixtures thereof.

According to one preferred embodiment, the gelling polymer is chosen from optionally modified polymers of natural origin, in particular guar gum.

According to one preferred embodiment, the gelling polymer is chosen from acrylic or methacrylic acid homopolymers or copolymers or salts and esters thereof, polyacrylic acids and polyacrylic acid salts, or mixtures thereof.

According to one preferred embodiment, the gelling polymer is a sodium salt of polyacrylic acid, especially a crosslinked sodium polyacrylate.

According to one particularly preferred embodiment, the gelling agent is chosen from associative polymers.

According to another particularly preferred embodiment, the gelling agent is chosen from natural polymers, optionally modified.

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, advantageously by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2OB_nR \qquad (I)$$

in which R' denotes H or $CH_3$, B denotes the ethyleneoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms.

Anionic amphiphilic polymers of this type are described and prepared, according to an emulsion polymerization process, in patent EP-0 216 479.

Among the associative anionic polymers that may also be mentioned are maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

Among the associative anionic polymers, it is possible, according to one preferred embodiment, to use copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 EO units) terpolymer or Aculyn 28 (methacrylic acid/ethyl acrylate/oxyethylenated behenyl methacrylate (25 EO) terpolymer).

Examples of associative anionic polymers that may also be mentioned include anionic polymers comprising at least one hydrophilic unit of unsaturated olefinic carboxylic acid type, and at least one hydrophobic unit exclusively of the type such as a ($C_{10}$-$C_{30}$) alkyl ester of an unsaturated carboxylic acid. Examples that may be mentioned include the anionic polymers described and prepared according to U.S. Pat. Nos. 3,915,921 and 4,509,949.

Cationic Associative Polymers

Cationic associative polymers that may be mentioned include quaternized cellulose derivatives and polyacrylates bearing amine side groups.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The polyacrylates bearing quaternized or non-quaternized amine side groups contain, for example, hydrophobic groups of the type such as steareth-20 (polyoxyethylenated (20) stearyl alcohol).

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X529-18-A, Quatrisoft LM-X529-18B ($C_{12}$ alkyl) and Quatrisoft LM-X529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Examples of polyacrylates bearing amino side chains that may be mentioned are the polymers 8781-121B or 9492-103 from the company National Starch.

Nonionic Associative Polymers

The nonionic associative polymers may be chosen from:
celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS($C_{16}$ alkyls) sold by the company Aqualon,
celluloses modified with alkylphenyl polyalkylene glycol ether groups, such as the product Amercell Polymer HM1500 (nonylphenyl polyethylene glycol (15) ether) sold by the company Amerchol,
guars such as hydroxypropyl guar, modified with groups comprising at least one fatty chain such as an alkyl chain,
copolymers of vinylpyrrolidone and of fatty-chain hydrophobic monomers,
copolymers of $C_1$-$C_6$ alkyl methacrylates or acrylates and of amphiphilic monomers comprising at least one fatty chain,
copolymers of hydrophilic methacrylates or acrylates and of hydrophobic monomers comprising at least one fatty chain, for instance the polyethylene glycol methacrylate/lauryl methacrylate copolymer,
associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be included. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a nonionic associative polymer of polyurethane type is used as gelling agent.

By way of example of polyurethane polyethers that may not be used in the invention, mention may be made of the polymer $C_{16}OE_{120}$-$C_{16}$ from the company Servo Delden (under the name SER AD FX1100, which is a molecule containing a urethane function and having a weight-average molecular weight of 1300), OE being an oxyethylene unit. Rheolate 205 bearing a urea function, sold by the company Rheox, or Rheolate 208 or 204, or alternatively Rheolate FX 1100 by Elementis, may also be used as associative polyurethane polymer. These associative polyurethanes are sold in pure form. The product DW 1206B from Röhm & Haas containing a $C_{20}$ alkyl chain and a urethane bond, sold at a solids content of 20% in water, may also be used.

It is also possible to use solutions or dispersions of these polymers, especially in water or in aqueous-alcoholic medium. Examples of such polymers that may be mentioned include SER AD FX1010, SER AD FX1035 and SER AD FX1070 from the company Servo Delden, and Rheolate 255, Rheolate 278 and Rheolate 244 sold by the company Rheox. It is also possible to use the products Aculyn 46, DW 1206F and DW 1206J, and also Acrysol RM 184 or Acrysol 44 from the company Röhm & Haas, or alternatively Borchigel LW 44 from the company Borchers, and mixtures thereof.

According to one preferred embodiment, the hydrophilic gelling agent is chosen from:
optionally modified hydroxypropyl guar, in particular hydroxypropyl guar modified with sodium methylcarboxylate groups (Jaguar XC97-1, Rhodia) or hydroxypropyltrimethylammonium guar chloride,
vinyl polymers, such as polyvinyl alcohol,
anionic associative polymers derived from (meth)acrylic acid, such as the non-crosslinked copolymer obtained from methacrylic acid and steareth-20 methacrylate, sold under the name Aculyn 22 by Röhm & Haas,
nonionic associative polymers of polyurethane polyether type, such as Steareth-100/PEG-136/HDI Copolymer sold under the name Rheolate FX 1100 by Elementis.

According to one preferred embodiment, the hydrophilic gelling agent is chosen from:
optionally modified hydroxypropyl guar, in particular hydroxypropyl guar modified with sodium methylcarboxylate groups (Jaguar XC97-1, Rhodia) or hydroxypropyltrimethylammonium guar chloride,
anionic associative polymers derived from (meth)acrylic acid, such as the non-crosslinked copolymer obtained from methacrylic acid and steareth-20 methacrylate, sold under the name Aculyn 22 by Röhm & Haas, nonionic associative polymers of polyurethane polyether type, such as Steareth-100/PEG-136/HDI Copolymer sold under the name Rheolate FX 1100 by Elementis.

Amphoteric Associative Polymers

Among the associative amphoteric polymers of the invention, mention may be made of crosslinked or non-crosslinked, branched or unbranched amphoteric polymers, which may be obtained by copolymerization 1) of at least one monomer of formula (IVa) or (IVb):

$$R_4-\underset{H}{\overset{}{C}}=\underset{R_5}{\overset{}{C}}-\underset{O}{\overset{}{C}}-Z-(C_nH_{2n})-\underset{R_6}{\overset{R_8 \quad A^-}{\overset{|}{N^+}}}-R_7 \quad (IVa)$$

$$R_4-\underset{H}{\overset{}{C}}=\underset{R_5}{\overset{}{C}}-\underset{O}{\overset{}{C}}-Z-(C_nH_{2n})-N\underset{R_7}{\overset{R_6}{\diagup}} \quad (IVb)$$

in which $R_4$ and $R_5$, which may be identical or different, represent a hydrogen atom or a methyl radical, $R_6$, $R_7$ and $R_8$, which may be identical or different, represent a linear or branched alkyl radical containing from 1 to 30 carbon atoms, Z represents a group NH or an oxygen atom, n is an integer from 2 to 5, $A^-$ denotes an anion derived from a mineral or organic acid, such as a methosulfate anion or a halide such as chloride or bromide.

$$R_9-\underset{H}{\overset{}{C}}=CR_{10}-CO-Z_1 \quad (V)$$

in which $R_9$ and $R_{10}$, which may be identical or different, represent a hydrogen atom or a methyl radical;

$Z_1$ represents a group OH or a group NHC(CH$_3$)$_2$CH$_2$SO$_3$H;

3) of at least one monomer of formula (VI):

$$R_9-\underset{H}{\overset{}{C}}=CR_{10}-COXR_{11} \quad (VI)$$

in which $R_9$ and $R_{10}$, which may be identical or different represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent; at least one of the monomers of formula (IVa), (IVb) or (VI) comprising at least one fatty chain containing from 8 to 30 carbon atoms and the said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group formed by:

dimethylaminoethyl methacrylate, dimethylaminoethyl acrylate, dimethylaminoethyl methacrylate, dimethylaminoethyl acrylate, dimethylaminopropyl methacrylate, dimethylaminopropyl acrylate, dimethylaminopropylmethacrylamide or dimethylaminopropylacrylamide, optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyltrimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers represents a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

The hydrophilic gelling polymer(s), and in particular the associative polymers, may be present in the composition according to the invention in a total active material content ranging from 0.1% to 10% by weight and preferably from 0.5% to 5% by weight relative to the total weight of the composition.

It is understood that this amount is moreover liable to vary depending on whether the said polymer is or is not combined with an ionic and/or nonionic surfactant and/or a film-forming agent (other than alkylcellulose and in particular ethylcellulose), which are themselves also capable of acting on the consistency of the said composition.

Silicone Gum

According to one particular embodiment, a composition of the invention may also comprise at least one silicone gum, preferably with a viscosity of between 800 000 and 10 000 000 cSt at 25° C.

Preferably, the silicone gum is chosen from silicone gums with a viscosity at 25° C. of between 1 000 000 and 5 000 000 cSt and preferably between 1 000 000 and 2 500 000 cSt. The viscosity of this silicone compound may be measured according to standard ASTM D-445.

The molecular mass of the silicone gums is generally greater than 350 000 g/mol, between 350 000 and 800 000 g/mol and preferably from 450 000 to 700 000 g/mol.

The silicone gum may be chosen especially from the silicones of formula:

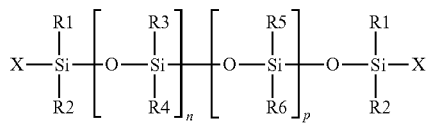

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p being integers chosen such that the viscosity of the compound is greater than 800 000 cSt.

As silicone gums that may be used according to the invention, mention may be made of those for which:
the substituents $R_1$ to $R_6$ represent a methyl group, the group X represents a methoxy group, and n and p are such that the molecular weight of the polymer is 600 000 g/mol, such as the product sold under the name Mirasil C-DPDM by the company Bluestar;
the substituents $R_1$ to $R_6$ represent a methyl group, the group X represents a hydroxyl group, and n and p are such that the molecular weight of the polymer is 600 000 g/mol, such as the product sold under the name SGM 36 by the company Dow Corning;
dimethicones of the (polydimethylsiloxane) (methylvinylsiloxane) type, such as SE63 sold by GE Bayer Silicones, poly(dimethylsiloxane)(diphenyl)(methylvinylsiloxane) copolymers, and mixtures thereof.

Advantageously, a composition according to the invention may comprise from 0.1% to 20% by weight of silicone gum(s) according to the invention relative to the total weight of the composition.

In particular, it may comprise from 0.2% to 15% by weight of silicone gum(s) according to the invention relative to the total weight of the composition.

Advantageously, a composition according to the invention comprises at least one silicone gum and at least one alkylcellulose polymer in a silicone gum(s)/alkylcellulose polymer weight ratio of between 0.1 and 15 and more particularly from 0.5 to 10. Preferably, the silicone gum(s)/alkylcellulose polymer weight ratio is between 0.5 and 5.

According to one particular embodiment, a composition of the invention comprises:
between 4% and 30% by weight of alkylcellulose, preferably ethylcellulose,
between 15% and 50% by weight of water,
between 45% and 75% by weight of nonvolatile oils, and
between 0.5% and 12% of silicone gum.

Organopolysiloxane Elastomer

According to another particular embodiment, a composition according to the invention comprises at least one organopolysiloxane elastomer.

These particular elastomers, when present in a composition according to the invention, make it possible to obtain non-tacky and comfort properties (suppleness of the deposit) for the deposits formed on the lips or the skin from compositions comprising them.

The term "organopolysiloxane elastomer" means a supple, deformable organopolysiloxane with viscoelastic properties and especially the consistency of a sponge or a supple sphere. Its modulus of elasticity is such that this material withstands deformation and has limited stretchability and contractability. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolyzable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

Compound (A) is the base compound for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from methylhydrogenopolysiloxanes containing trimethylsiloxy end groups, dimethyl siloxane-methylhydrogenosiloxane copolymers containing trimethylsiloxy end groups, and dimethylsiloxane-methylhydrogenosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethyl siloxane-methyl(3,3,3-trifluoropropyl)siloxane copolymers containing dimethylvinylsiloxy end groups.

In particular, the organopolysiloxane elastomer may be obtained by reaction of a dimethyl polysiloxane containing dimethylvinylsiloxy end groups and of methylhydrogenopolysiloxane containing trimethylsiloxy end groups, in the presence of a platinum catalyst.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units.

The organopolysiloxane elastomer particles are conveyed in the form of a gel formed from an elastomeric organopolysiloxane included in at least one hydrocarbon-based oil and/or one silicone oil. In these gels, the organopolysiloxane particles are often nonspherical particles.

Non-emulsifying elastomers are especially described in patents EP 242 219, EP 285 886 and EP 765 656 and in patent application JP-A-61-194 009, the content of which is incorporated by way of reference.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

Spherical non-emulsifying elastomers that may be used include those sold under the names DC 9040, DC 9041, DC 9509, DC 9505 and DC 9506 by the company Dow Corning.

The elastomer may also be an emulsifying elastomer.

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

Preferably, the organopolysiloxane elastomer is obtained by crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for instance, in U.S. Pat. Nos. 5,236,986 and 5,412,004.

In particular, the organopolysiloxane may be obtained by reaction of polyoxyalkylene (especially polyoxyethylene and/or polyoxypropylene) with dimethylvinylsiloxy end groups and of methylhydrogenopolysiloxane with trimethylsiloxy end groups, in the presence of a platinum catalyst.

The organic groups bonded to the silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethyl siloxane-methylhydrogenosiloxane copolymers containing trimethylsiloxy end groups, dimethylsiloxane-methylhydrogenosiloxane cyclic copolymers, dimethyl siloxane-methylhydrogenosiloxane-laurylmethylsiloxane copolymers containing trimethylsiloxy end groups.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are especially described in U.S. Pat. Nos. 5,236,986, 5,412,004, 5,837,793 and 5,811,487, the content of which is incorporated by reference.

Polyoxyalkylenated organopolysiloxane elastomers that may be used include those sold under the names KSG-21, KSG-20, KSG-30, KSG-31, KSG-32, KSG-33, KSG-210, KSG-310, KSG-320, KSG-330 and KSG-340 by the company Shin-Etsu, and DC9010 and DC9011 by the company Dow Corning.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

Preferably, the organopolysiloxane elastomer is obtained by crosslinking addition reaction (A2) of diorganopolysiloxane containing at least two hydrogens each bonded to a silicon, and (B2) of glycerolated compounds containing at least two ethylenically unsaturated groups, especially in the presence (C2) of a platinum catalyst.

In particular, the organopolysiloxane may be obtained by reaction of a polyglycerolated compound with dimethylvinylsiloxy end groups and of methylhydrogenopolysiloxane with trimethylsiloxy end groups, in the presence of a platinum catalyst.

Compound (A2) is the base reagent for the formation of an organopolysiloxane elastomer, and the crosslinking is performed by addition reaction of compound (A2) with compound (B2) in the presence of the catalyst (C2).

Compound (A2) is in particular an organopolysiloxane containing at least two hydrogen atoms bonded to different silicon atoms in each molecule.

Compound (A2) may have any molecular structure, especially a linear-chain or branched-chain structure or a cyclic structure.

Compound (A2) may have a viscosity at 25° C. ranging from 1 to 50 000 centistokes, especially so as to be miscible with compound (B2).

The organic groups bonded to the silicon atoms in compound (A2) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Preferably, said organic group is chosen from methyl, phenyl and lauryl groups.

Compound (A2) may thus be chosen from methylhydrogenopolysiloxanes containing trimethylsiloxy end groups, dimethyl siloxane-methylhydrogenosiloxane copolymers containing trimethylsiloxy end groups, dimethylsiloxane-methylhydrogenosiloxane cyclic copolymers and dimethyl siloxane-methylhydrogenosiloxane-laurylmethylsiloxane copolymers containing trimethylsiloxy end groups.

Compound (B2) may be a polyglycerolated compound corresponding to formula (B') below:

$$C_mH_{2m-1}-O-[Gly]_n-C_mH_{2m-1} \tag{B'}$$

in which m is an integer ranging from 2 to 6, n is an integer ranging from 2 to 200, preferably from 2 to 100, preferably ranging from 2 to 50, preferably ranging from 2 to 20, preferably ranging from 2 to 10 and preferentially ranging from 2 to 5, and in particular n is equal to 3; Gly denotes:

$$-CH_2-CH(OH)-CH_2-O- \text{ or } -CH_2-CH(CH_2OH)-O-$$

Advantageously, the sum of the number of ethylenic groups per molecule in compound (B2) and of the number of hydrogen atoms bonded to silicon atoms per molecule in compound (A2) is at least 4.

It is advantageous for compound (A2) to be added in an amount such that the molecular ratio between the total amount of hydrogen atoms bonded to silicon atoms in compound (A2) and the total amount of all the ethylenically unsaturated groups in compound (B2) is within the range from 1/1 to 20/1.

Compound (C2) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

The polyglycerolated organopolysiloxane elastomer according to the invention is conveyed in gel form in at least one hydrocarbon-based oil and/or one silicone oil. In these gels, the polyglycerolated elastomer is often in the form of nonspherical particles.

Polyglycerolated organopolysiloxane elastomers that may be used include those sold under the names KSG-710, KSG-810, KSG-820, KSG-830 and KSG-840 by the company Shin-Etsu.

Advantageously, the organopolysiloxane elastomer under consideration according to the invention is chosen from spherical non-emulsifying organopolysiloxane elastomers, polyglycerolated organopolysiloxane elastomers and polyoxyalkylenated organopolysiloxane elastomers.

Emulsifying elastomers that may be used more particularly include those sold under the names KSG-31, KSG-32, KSG-33, KSG-210 and KSG-710 by the company Shin-Etsu.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

Preferably, the silicone elastomer is non-emulsifying, for example in the case of lipstick compositions, and in particular in the case of anhydrous compositions.

The composition according to the invention may comprise an organopolysiloxane elastomer, alone or as a mixture, in a content ranging from 0.1% to 20% by weight, preferably from 0.2% to 15% by weight and even more preferably from 0.5% to 12% by weight.

It is understood that, in the context of the present invention, the weight percentages of a compound are always expressed as weight of solids of the compound in question.

Advantageously, the alkylcellulose polymer according to the invention and the organopolysiloxane elastomer are used in an organopolysiloxane elastomer(s)/alkylcellulose weight ratio ranging from 0.1 to 15 and more particularly from 0.5 to 10. Preferably, the organopolysiloxane elastomer(s)/alkylcellulose weight ratio is between 0.5 and 5.

As stated above, the elastomer is generally used with a fatty phase.

According to one particular embodiment, a composition of the invention comprises:
  between 4% and 30% by weight of alkylcellulose, preferably ethylcellulose,
  between 15% and 50% by weight of water,
  between 45% and 75% by weight of nonvolatile oils, and
  between 0.5% and 12% of organopolysiloxane elastomer(s).

Silicone Resin

According to another particular embodiment, a composition according to the invention comprises at least one silicone resin.

More generally, the term "resin" means a compound whose structure is three-dimensional. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters "MDTQ" characterizing a type of unit.

The letter M represents the monofunctional unit of formula R1R2R3 $SiO_{1/2}$, the silicon atom being bonded to only one oxygen atom in the polymer comprising this unit.

The letter D means a difunctional unit R1R2$SiO_{2/2}$ in which the silicon atom is bonded to two oxygen atoms.

The letter T represents a trifunctional unit of formula R1 $SiO_{3/2}$.

Such resins are described, for example, in the *Encyclopedia of Polymer Science and Engineering*, vol. 15, John Wiley & Sons, New York, (1989), pp. 265-270, and U.S. Pat. Nos. 2,676,182, 3,627,851, 3,772,247, 5,248,739 or U.S. Pat. Nos. 5,082,706, 5,319,040, 5,302,685 and 4,935,484.

In the units M, D and T defined previously, R, namely R1 and R2, represents a hydrocarbon-based radical (especially alkyl) containing from 1 to 10 carbon atoms, a phenyl group, a phenylalkyl group or a hydroxyl group.

Finally, the letter Q means a tetrafunctional unit $SiO_{4/2}$ in which the silicon atom is bonded to four hydrogen atoms, which are themselves bonded to the rest of the polymer.

Various silicone resins with different properties may be obtained from these different units, the properties of these polymers varying as a function of the type of monomer (or unit), the nature and number of the radical R, the length of the polymer chain, the degree of branching and the size of the pendent chains.

As silicone resins that may be used in the compositions according to the invention, use may be made, for example, of silicone resins of MQ type, of T type or of MQT type.

According to one preferred embodiment, an MQ resin is used.

MQ resins:

As examples of silicone resins of MQ type, mention may be made of the alkyl siloxysilicates of formula $[(R1)_3 SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethyl siloxysilicate type, mention may be made of those sold under the reference SR1000 by the company General Electric, under the reference TMS 803 by the company Wacker, or under the name KF-7312J by the company Shin-Etsu or DC 749 or DC 593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in U.S. Pat. No. 5,817,302.

T Resins:

Examples of silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or by the company Shin-Etsu under the reference KR220L, which are composed of units T of formula $CH_3SiO_{3/2}$ and have Si—OH (silanol) end groups, under the reference KR242A, which comprise 98% of units T and 2% of dimethyl units D and have Si—OH end groups, or alternatively under the reference KR251 comprising 88% of units T and 12% of dimethyl units D and have Si—OH end groups.

MQT Resins:

Resins comprising MQT units that are especially known are those mentioned in document U.S. Pat. No. 5,110,890.

A preferred form of resins of MQT type are MQT-propyl (also known as MQTpr) resins. Such resins that may be used in the compositions according to the invention are especially the resins described and prepared in patent application WO 2005/075 542, the content of which is incorporated herein by reference.

The MQ-T-propyl resin preferably comprises the following units:
(i) $(R1_3SiO_{1/2})_a$
(ii) $(R2_2SiO_{2/2})_b$
(iii) $(R3SiO_{3/2})_c$ and
$(SiO_{4/2})_d$
with
R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group,
a being between 0.05 and 0.5,
b being between 0 and 0.3,
c being greater than 0,
d being between 0.05 and 0.6,
a+b+c+d=1, and a, b, c and d being mole fractions,
on condition that more than 40 mol % of the groups R3 of the siloxane resin are propyl groups.

Preferably, the siloxane resin comprises the following units:
(i) $(R1_3SiO_{1/2})_a$
(iii) $(R3SiO_{3/2})_c$ and
(iv) $(SiO_{4/2})_d$
with
R1 and R3 independently representing an alkyl group containing from 1 to 8 carbon atoms, R1 preferably being a methyl group and R3 preferably being a propyl group,
a being between 0.05 and 0.5 and preferably between 0.15 and 0.4,
c being greater than zero, preferably between 0.15 and 0.4,
d being between 0.05 and 0.6, preferably between 0.2 and 0.6 or alternatively between 0.2 and 0.55,
a+b+c+d=1, and a, b, c and d being mole fractions,
on condition that more than 40 mol % of the groups R3 of the siloxane resin are propyl groups.

The siloxane resins that may be used according to the invention may be obtained via a process comprising the reaction of:
A) an MQ resin comprising at least 80 mol % of units $(R1_3SiO_{1/2})_a$ and $(SiO_{4/2})_d$,
R1 representing an alkyl group containing from 1 to 8 carbon atoms, an aryl group, a carbinol group or an amino group,
a and d being greater than zero,
the ratio a/d being between 0.5 and 1.5;
and
B) a T-propyl resin comprising at least 80 mol % of units $(R3SiO_{3/2})_c$,
R3 representing an alkyl group containing from 1 to 8 carbon atoms, an aryl group, a carbinol group or an amino group,
c being greater than 0,
on condition that at least 40 mol % of the groups R3 are propyl groups,
in which the mass ratio A/B is between 95/5 and 15/85 and preferably the mass ratio A/B is 30/70.

Advantageously, the mass ratio A/B is between 95/5 and 15/85. Preferably, the ratio A/B is less than or equal to 70/30. These preferred ratios have proven to allow comfortable deposits due to the absence of percolation of the rigid particles of MQ resin in the deposit.

Thus, preferably, the silicone resin is chosen from the group comprising:
a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or
b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, said polysilsesquioxanes also possibly comprising Si—OH end groups, and/or
c) a resin of MQT type, especially of MQT-propyl type, which may comprise units (i) $(R1_3SiO_{1/2})_a$, (R2$_2$SiO$_{2/2}$)$_b$, (iii) $(R3SiO_{3/2})_c$ and (iv) $(SiO_{4/2})_d$,
with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group,
a being between 0.05 and 0.5,
b being between 0 and 0.3,
c being greater than 0,
d being between 0.05 and 0.6,
a+b+c+d=1, and a, b, c and d being mole fractions,
on condition that more than 40 mol % of the groups R3 of the siloxane resin are propyl groups.

Preferably, the silicone resin is present in the first composition according to the invention in a total content of resin solids ranging from 0.5% to 20% by weight and preferably ranging from 1% to 10% by weight relative to the total weight of the composition.

Advantageously, a composition according to the invention comprises at least one silicone resin and at least one alkylcellulose polymer in a silicone resin/alkylcellulose polymer weight ratio of between 0.05 and 15 and more particularly from 0.1 to 10. Preferably, the silicone resin/alkylcellulose polymer weight ratio is between 0.3 and 5.

According to one particular embodiment, a composition of the invention comprises:
between 4% and 30% by weight of alkylcellulose, preferably ethylcellulose,
between 15% and 50% by weight of water,
between 45% and 75% by weight of nonvolatile oils, and
between 1% and 10% of silicone resin.

Active Agents

The composition may also comprise at least one active agent chosen from moisturizers, cicatrizing agents and/or anti-ageing agents, for the skin and/or the lips, and in particular the lips.

According to this embodiment, the invention also relates to a process for caring for the skin and/or the lips, and in particular the lips, comprising the application of a composition according to the invention to the skin and/or the lips.

According to another of its aspects, the invention relates to a lip balm (liquid or solid) or lipstick formed from a composition according to the invention also comprising at least one active agent chosen from moisturizers, cicatrizing agents and/or antiaging agents.

Since the deposit made with a composition according to the invention has a good level of wear property, this ensures the remanence of the active agent on the skin and/or the lips and thus improves the care efficacy (moisturizing, cicatrizing and/or anti-ageing effect) on the skin and/or the lips.

Moisturizers:

According to a first embodiment, the composition also comprises at least one moisturizer (also known as a humectant).

Moisturizers or humectants that may especially be mentioned include sorbitol, polyhydric alcohols, preferably of $C_2$-$C_8$ and more preferably $C_3$-$C_6$, preferably such as glycerol, propylene glycol, 1,3-butylene glycol, dipropylene glycol and diglycerol, and mixtures thereof, glycerol and derivatives thereof, urea and derivatives thereof, especially Hydrovance® (2-hydroxyethylurea) sold by National Starch, lactic acids, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* sold under the name Moist 24® by the company Sederma, acrylic acid homopolymers, for instance Lipidure-HM® from NOF Corporation, beta-glucan and in particular sodium carboxymethyl beta-glucan from Mibelle-AG-Biochemistry; a mixture of passionflower oil, apricot oil, corn oil and rice bran oil sold by Nestle under the name NutraLipids®; a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product sold by Chimex under the trade name Mexoryl SBB®; an oil of musk rose sold by Nestle; an extract of the microalga Prophyridium cruentum enriched with zinc, sold by Vincience under the name Algualane Zinc®; spheres of collagen and of chondroitin sulfate of marine origin (Atelocollagen) sold by the company Engelhard Lyon under the name Marine Filling Spheres; hyaluronic acid spheres such as those sold by the company Engelhard Lyon; and arginine.

Use will preferably be made of a moisturizer chosen from glycerol, urea and derivatives thereof, especially Hydrovance® sold by National Starch, hyaluronic acid, AHAs, BHAs, acrylic acid homopolymers, for instance Lipidure-HM® from NOF Corporation, beta-glucan and in particular sodium carboxymethyl beta-glucan from Mibelle-AG-Biochemistry; a mixture of passion flower oil, apricot oil, corn oil and rice bran oil sold by Nestlé under the name NutraLipids®; a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product sold by Chimex under the trade name Mexoryl SBB®; an oil of musk rose sold by Nestle; an extract of the microalga Prophyridium cruentum enriched with zinc, sold by Vincience under the name Algualane Zinc®; spheres of collagen and of chondroitin sulfate of marine origin (Atelocollagen) sold by the company Engelhard Lyon under the name Marine Filling Spheres; hyaluronic acid spheres such as those sold by the company Engelhard Lyon; and arginine.

Cicatrizing Agents

The active agent may also be chosen from cicatrizing agents.

Examples of cicatrizing agents that may especially be mentioned include: allantoin, urea, certain amino acids, for instance hydroxyproline, arginine, and serine, and also extracts of white lily (for instance Phytélène Lys 37EG 16295 from Indena), a yeast extract, for instance the cicatrizing agent LS LO/7225B from Laboratoires Sérobiologiques) (Cognis), tamanu oil, extract of *Saccharomyces cerevisiae*, for instance Biodynes® TRF® from Arch Chemical, oat extracts, chitosan and derivatives, for instance chitosan glutamate, carrot extracts, artemia extract, for instance GP4G® from Vincience, sodium acexamate, lavandin extracts, propolis extracts, ximeninic acid and salts thereof, rose hip oil, marigold extracts, for instance Souci Ami® Liposolible from Alban Muller, horsetail extracts, lemon peel extracts, for instance Herbasol® citron from Cosmetochem, *helichrysum* extracts, common yarrow extracts, folic acid, beta-glucan derivatives, shea butter and purified fractions thereof, modified exopolysaccharides and alkylsulphone polyaminosaccharides.

Anti-Ageing Agents

The active agent may also be chosen from anti-ageing agents, i.e. agents especially having a restructuring effect on the skin barrier, anti-glycation agents, active agents that stimulate the energy metabolism of cells, and mixtures thereof.

The agent with a restructuring effect on the skin barrier may be chosen from an extract of *Thermus thermophilus* such as Vénucéane® from Sederma, an extract of the rhizome of wild yam (*Dioscorea villosa*) such as Actigen Y® from Active Organics, plankton extracts, for instance Omega Plankton® from Secma, yeast extracts, for instance Relipidium® from Coletica, a chestnut extract such as Recoverine® from Silab, a cedar bud extract such as Gatuline Zen® from Gattefossé, sphingosines, for instance salicyloyl sphingosine sold under the name Phytosphingosine® SLC by the company Degussa, a mixture of xylitol, polyxylityl glycoside and xylitan, for instance Aquaxyl® from SEPPIC, extracts of Solanacea plants, for instance Lipidessence® from Coletica, and mixtures thereof.

Mention may also be made especially of ceramides, sphingoid-based compounds, glycosphingolipids, phospholipids, cholesterol and derivatives thereof, phytosterols, essential fatty acids, diacylglycerol, 4-chromanone and chromone derivatives, and mixtures thereof.

As preferred agents having a restructuring effect on the skin barrier function, mention will be made of an extract of *Thermus thermophilus*, an extract of the rhizome of wild yam (*Dioscorea villosa*), a yeast extract, a chestnut extract, a cedar bud extract, and mixtures thereof.

The term "anti-glycation agent" means a compound that prevents and/or reduces the glycation of skin proteins, in particular dermal proteins such as collagen.

Examples of anti-glycation agents include extracts of plants of the Ericacea family, such as an extract of blueberry (*Vaccinium angustifolium* or *Vaccinium myrtillus*), for example the product sold under the name Blueberry Herbasol Extract PG by the company Cosmetochem, ergothioneine and derivatives thereof, hydroxystilbenes and derivatives thereof, such as resveratrol and 3,3',5,5'-tetrahydroxystilbene (these anti-glycation agents are described in patent applications FR 2 802 425, FR 2 810 548, FR 2 796 278 and FR 2 802 420, respectively), dihydroxystilbenes and derivatives thereof, polypeptides of arginine and of lysine such as the product sold under the name Amadorine® by the company Solabia, carcinine hydrochloride (sold by Exsymol under the name Alistin®), an extract of *Helianthus annuus*, for instance Antiglyskin® from Silab, wine extracts such as the extract of powdered white wine on a maltodextrin support sold under the name Vin blanc déshydraté 2F by the company Givaudan, thioctic acid (or alpha-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

The active agent for stimulating the energy metabolism of cells may be chosen, for example, from biotin, an extract of *Saccharomyces cerevisiae* such as Phosphovital® from Sederma, the mixture of sodium, manganese, zinc and magnesium salts of pyrrolidonecarboxylic acid, for instance Physiogenyl® from Solabia, a mixture of zinc, copper and magnesium gluconate, such as Sepitonic M3® from SEPPIC, and mixtures thereof.

The active agents used in the compositions according to the invention may be hydrophilic or lipophilic.

Preferably, the composition comprises at least one hydrophilic active agent, chosen from moisturizers, cicatrizing agents and anti-ageing agents.

Specifically, since the composition according to the invention comprises water, this water lends itself particularly to the introduction of hydrophilic active agents into the composition, in particular without any problem of stability of the composition and/or of the active agent. This is particularly interesting, in particular in the context of lipcare. Specifically, the standard lipstick compositions known in the prior art, whether they are solid or liquid, rarely comprise water, and, if they do contain any, they are generally unstable over time (i.e. they undergo phase separation or exudation).

Preferably, the active agent is chosen from: polyhydric alcohols, preferably of $C_2$-$C_8$ and more preferably of $C_3$-$C_6$, preferably such as glycerol, propylene glycol, 1,3-butylene glycol, dipropylene glycol, diglycerol, and a mixture thereof, hyaluronic acid, AHAs, BHAs, serine, collagen, a C-glycoside derivative and in particular C-β-D-xylopyranoside-2-hydroxypropane in the form of a solution containing 30% by weight active material in a water/propylene glycol mixture (60/40 wt %); spheres of collagen and of chondroitin sulfate of marine origin (atelocollagen), hyaluronic acid spheres; ceramides, preferably such as ceramide V.

Preferably, the active material content of the composition ranges from 0.001% to 30% by weight, preferably from 0.01% to 20% by weight, better still from 0.01% to 10% by weight, better still from 0.01% to 5% by weight and even better still from 0.05% to 1% by weight relative to the total weight of the composition.

A composition according to the invention may also comprise any additional component usually used in cosmetics, such as dyestuffs, fillers or cosmetic active agents.

Needless to say, a person skilled in the art will take care to select the optional additional compounds and/or the amount thereof such that the advantageous properties of the composition used according to the invention are not, or are not substantially, adversely affected by the envisaged addition.

Dyestuffs

A composition in accordance with the present invention may comprise at least one dyestuff, which may be chosen from water-soluble or water-insoluble, liposoluble or non-liposoluble, organic or mineral dyestuffs, and materials with an optical effect, and mixtures thereof.

For the purposes of the present invention, the term "dyestuff" means a compound that is capable of producing a coloured optical effect when it is formulated in sufficient amount in a suitable cosmetic medium.

According to one preferred embodiment, a composition according to the invention comprises at least one water-soluble dyestuff.

The water-soluble dyestuffs used according to the invention are more particularly water-soluble dyes.

For the purposes of the invention, the term "water-soluble dye" means any natural or synthetic, generally organic compound, which is soluble in an aqueous phase or water-miscible solvents and which is capable of colouring. In particular, the term "water-soluble" means the capacity of a compound to be dissolved in water, measured at 25° C., to a concentration at least equal to 0.1 g/l (production of a macroscopically isotropic, transparent, coloured or colourless solution). This solubility is in particular greater than or equal to 1 g/l.

As water-soluble dyes that are suitable for use in the invention, mention may be made especially of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), FDC Yellow 8 (CI: 45350 Na salt), FDC Green 3 (CI: 42053), DC Green 5 (CI: 61570), FDC Blue 1 (CI: 42090).

As non-limiting illustrations of sources of water-soluble dyestuffs that may be used in the context of the present invention, mention may be made especially of those of natural origin, such as extracts of cochineal carmine, of beetroot, of grape, of carrot, of tomato, of annatto, of paprika, of henna, of caramel and of curcumin.

Thus, the water-soluble dyestuffs that are suitable for use in the invention are especially carminic acid, betanin, anthocyans, enocyanins, lycopene, beta-carotene, bixin, norbixin, capxanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, methylene blue, the disodium salt of tartrazine and the disodium salt of fuchsin.

Some of these water-soluble dyestuffs are especially permitted for food use. Representatives of these dyes that may be mentioned more particularly include dyes of the carotenoid family, referenced under the food codes E120, E162, E163, E160a-g, E150a, E101, E100, E140 and E141.

According to one preferred variant, the water-soluble dyestuff(s) that are to be transferred onto the skin and/or the lips intended to be made up are formulated in a physiologically acceptable medium so as to be compatible with impregnation into the substrate.

The water-soluble dyestuff(s) may be present in a composition according to the invention in a content ranging from 0.01% to 8% by weight and preferably from 0.1% to 6% by weight relative to the total weight of the said composition.

According to a particularly preferred embodiment, the water-soluble dyestuff(s) are chosen from the disodium salt of brilliant yellow FCF sold by the company LCW under the name DC Yellow 6, the disodium salt of fuchsin acid D sold by the company LCW under the name DC Red 33, and the trisodium salt of Rouge Allura sold by the company LCW under the name FD & C Red 40.

According to one particular embodiment of the invention, the composition according to the invention comprises only water-soluble dyes as dyestuffs.

According to another embodiment, a composition according to the invention may comprise, besides the water-soluble dyestuffs described previously, one or more additional dyestuffs, especially such as pigments or nacres, conventionally used in cosmetic compositions.

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof.

The organic pigments may be, for example:
cochineal carmine,
organic pigments of azo dyes, anthraquinone dyes, indigoid dyes, xanthene dyes, pyrene dyes, quinoline dyes, triphenylmethane dyes and fluorane dyes;
organic lakes or insoluble sodium, potassium, calcium, barium, aluminium, zirconium, strontium or titanium salts of acidic dyes such as azo, anthraquinone, indigoid, xanthene, pyrene, quinoline, triphenylmethane or fluorane dyes, These dyes generally comprise at least one carboxylic or sulfonic acid group;
melanin-based pigments.

Among the organic pigments, mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 and FD&C Yellow No. 6.

The hydrophobic treatment agent may be chosen from silicones such as methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkyl silanes, perfluoroalkyl silazanes, polyhexafluoropropylene oxides, polyorganosiloxanes comprising perfluoroalkyl perfluoropolyether groups, amino acids, N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above especially denotes an alkyl group containing from 1 to 30 carbon atoms and preferably containing from 5 to 16 carbon atoms.

Hydrophobic-treated pigments are described especially in patent application EP-A-1 086 683.

For the purposes of the present patent application, the term "nacre" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or tint.

As illustrations of nacres that may be introduced as interference pigments into the first composition, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

According to one particular embodiment, the composition according to the invention is free of dyestuff. According to this embodiment, the composition is advantageously a colorless lipcare balm, which may be in liquid or solid form, preferably in liquid form.

Fillers

A cosmetic composition used according to the invention may also comprise at least one filler, of organic or mineral nature.

The term "filler" should be understood as meaning colourless or white solid particles of any form, which are in an insoluble form and dispersed in the medium of the composition. These particles, of mineral or organic nature, can give body or rigidity to the composition and/or softness and uniformity to the makeup. They are different from dyestuffs.

The fillers may be mineral or organic and of any form, platelet-shaped, spherical or oblong, irrespective of the crystallographic form (for example lamellar, cubic, hexagonal, orthorhombic, etc.). In particular, the filler may be chosen from talc, mica, silica, kaolin, bentone, fumed silica particles, optionally hydrophilic- or hydrophobic-treated, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), precipitated calcium carbonate, magnesium carbonate, magnesium hydrogen carbonate, hydroxyapatite, hollow silica microspheres (Silica Beads® from Maprecos), elastomeric polyorganosiloxane particles, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and mixtures thereof.

Preferably, the filler is chosen from silica, kaolin, bentone, starch, lauroyllysine, and fumed silica particles, optionally hydrophilic- or hydrophobic-treated, and mixtures thereof.

A composition used according to the invention may comprise one or more fillers in a content ranging from 0.1% to 15% by weight relative to the total weight of the composition and in particular from 1% to 10% by weight relative to the total weight of the composition.

Preferably, a composition according to the invention comprises at least one compound chosen from fillers, waxes, pasty fatty substances, semi-crystalline polymers and/or lipophilic gelling agents, and mixtures thereof.

Usual Additional Cosmetic Ingredients

A composition used according to the invention may also comprise any usual cosmetic ingredient, which may be chosen especially from antioxidants, additional film-forming polymers (lipophilic or hydrophilic) other than alkylcellulose and in particular ethylcellulose, fragrances, preserving agents, neutralizers, sunscreens, sweeteners, vitamins, free-radical scavengers and sequestrants, and mixtures thereof.

Needless to say, a person skilled in the art will take care to select the optional additional ingredients and/or the amount thereof such that the advantageous properties of the composition according to the invention are not, or are not substantially, adversely affected by the envisaged addition.

A composition according to the invention may more particularly be a composition for making up and/or caring for the skin and/or the lips, in particular the lips.

A composition according to the invention may constitute a liquid lipstick for the lips, a body makeup product, a facial or body care product or an antisun product.

According to one preferred embodiment, a composition of the invention is in liquid form. As illustrations of liquid formulations, mention may be made especially of lip glosses.

According to one particularly preferred embodiment, the composition according to the invention is an oil-in-water emulsion.

The composition according to the invention may be manufactured via the known processes generally used in cosmetics or dermatology.

As stated previously, the composition according to the invention is homogeneous and gives access to a deposit that has good cosmetic properties, in particular in terms of gloss, comfort (thin, light deposit) and absence of tackiness.

The terms "between" and "ranging from" should be understood as including the limits.

The present invention will be understood more clearly by means of the examples that follow.

These examples are given as illustrations of the invention and cannot be interpreted as limiting its scope.

EXAMPLES 1 AND 2: LIQUID LIP FORMULATIONS

| Ingredients | Compounds/Commercial Ref. | Example 1 according to the invention (weight %) | Example 2 according to the invention (weight %) |
|---|---|---|---|
| Dye | Disodium salt of fuchsin acid D (CI: 17200), disodium salt of tartrazine (CI: 19140) and trisodium salt of Allura Red (CI: 16035) | 0.2 | — |
| Aqueous dispersion of pigments | Red 7 (and) acrylic styrene copolymer (and) ammonium hydroxide | — | 1.22 |
| Glycol | Butylene glycol | — | 1.63 |
| Preserving agent | Phenoxyethanol | 0.5 | 0.5 |
| Non-volatile polar oil | Octyldodecanol | 33.35 | 35.75 |
| Dispersion of ethylcellulose in water | Ethylcellulose at 26.2% in water; sodium lauryl sulfate (1.3%) and cetyl alcohol (2.5%)/Aquacoat ECD 30 from FMC Biopolymer | 33.35* | 35.75* |
| Polymer | Polyvinyl alcohol (viscosity: 50/degree of hydrolysis: 88%)/Celvol 540 PV Alcohol from Celanese Chemicals | 0.5 | 1 |
| Silicone | Polyphenyltrimethylsiloxydimethylsiloxane (viscosity: 1000 cSt- MW: 3000 g/mol)/Wacker-Belsil PDM 1000 from Wacker | 23 | 19 |
| Solvent | Non-denatured 96-degree ethyl alcohol | 3 | 3 |
| Solvent | Water | 2.15 | 2.15 |
| Surfactant | Mixture of sorbitan stearate, sucrose cocoate/Arlatone 2121U from Croda | 3.95 | — |
| | Total | 100 | 100 |

*Expressed as weight of commercial product.

Preparation Protocol
1) The aqueous dispersion of ethylcellulose is mixed with the non-volatile polar oil with stirring, and the mixture is heated for 1 to 2 hours at 55° C.
2) The surfactant is added (for Example 1) and the mixture is stirred at 55° C. until homogeneous.
3) The polyvinyl alcohol is added until a homogeneous mixture is obtained, and the resulting mixture is left to cool to room temperature.
4) The non-volatile silicone oil is then added with continued stirring.
5) The dyes/pigments predissolved in water are then added.
6) Finally, the alcohol and the phenoxyethanol are added with stirring (for Example 1).

Evaluation of the Cosmetic Properties: Gloss, Migration Resistance

The gloss and the migration are evaluated in vivo by means of a Chromasphere SEI-M-02232-CHRO-0 as described in patent application FR 2 829 344.
The gloss is evaluated just after application of the formulation and then one hour after application.
The formulations are applied to the lips of a panel of six individuals with fleshy and light lips.

Protocol for Evaluating the Tack:

The tacky aspect of the deposits produced with the formulations was also evaluated according to the following protocol: A sample of each of the compositions was applied to the lips so as to form a deposit of uniform thickness.

The tacky nature on the finger was evaluated during drying of the formulation after 2 minutes at room temperature (25° C.). To do this, a finger was applied, after the specified drying time, onto the applied formula and the tack was assessed by the person on removal of his finger from the applied formulation.

The results obtained are collated in Table 1 below:

TABLE 1

|  | Tests | Formulation 1 | Formulation 2 |
|---|---|---|---|
| Gloss | Immediate gloss | 244 ± 9 | 234 ± 13 |
|  | Gloss at 1 hour | 248 ± 23 | 231 ± 19 |
|  | Migration | Very sparingly migrating | Very sparingly migrating |
|  | Tacky | Non-tacky | Non-tacky |

Result

The compositions of Examples 1 and 2 are applied to the lips. They are comfortable on application (easy to apply) and do not give a tacky sensation and migrate very sparingly.

The makeup deposit obtained is uniform, thin and light, has very good gloss and gloss remanence on the lips, and also satisfactory wear property of the colour.

EXAMPLES 3 AND 4: LIQUID LIPSTICKS

| Ingredients | Compounds/commercial refs. | Example 3 according to the invention (weight %) | Example 4 According to the invention (weight %) |
|---|---|---|---|
| Dispersion of ethylcellulose in water | Ethylcellulose at 26.2% in water; sodium lauryl sulfate (1.3%) and cetyl alcohol (2.5%) Aquacoat ECD 30 from FMC Biopolymer | 32.97 | 32.97 |
| Non-volatile polar oil | Octyldodecanol | 32.97 | 32.97 |
| Non-volatile oil | Trimethylsiloxyphenyl dimethicone/Belsil PDM 1000 from Wacker | 23 | — |
|  | Perfluoroperhydrophenanthrene/Fiflow 220 from F2 Chemicals | — | 23 |
| Preserving agents | Phenoxyethanol and ethanol | 3.5 | 3.5 |
| Solvent | Water | 2.76 | 2.76 |
| Thickener | Polyvinyl alcohol | 0.5 | 0.5 |
| Surfactant | Mixture of sorbitan stearate and sucrose cocoate (Arlatone 2121U from Croda) | 4 | 4 |
| Water-soluble dyes | Disodium salt of fuchsin acid D (CI: 17200), disodium salt of tartrazine (CI: 19140) and trisodium salt of Allura Red (CI: 16035) | 0.3 | 0.3 |
| Total: |  | 100 | 100 |

Preparation Protocol
1) The aqueous dispersion of ethylcellulose is mixed with the non-volatile polar oil with stirring, and the mixture is heated for 1 to 2 hours at 55° C.
2) The surfactant is added and the mixture is stirred at 55° C. until homogeneous.
3) The polyvinyl alcohol is added until a homogeneous mixture is obtained, and the resulting mixture is left to cool to room temperature.
4) The non-volatile silicone oil (Ex. 3) or fluoro oil (Ex. 4) or the triglyceride mixture (Ex. 5) is then added with continued stirring.
5) The dyes predissolved in water are then added.
6) Finally, the alcohol and the phenoxyethanol are added with stirring.

Result

|  | Example 3 according to the invention | Example 4 according to the invention |
|---|---|---|
| Appearance after 24 hours | Very fluid homogeneous cream | Very fluid homogeneous cream |
| Aspect under a microscope | Clean homogeneous dispersion | Clean homogeneous dispersion |

The compositions of Examples 3 and 4 are applied to the lips.

The application of the compositions of Examples 3 and 4 in accordance with the invention is easy and comfortable. The deposit affords a sensation of softness. The deposit produced with composition 3 according to the invention is non-tacky. The deposit produced with composition 4 is slightly tacky.

The compositions of Examples 3 and 4 produce a glossy uniform makeup on the lips and have a satisfactory level of wear property of the colour.

EXAMPLE 5 AND 6: LIQUID LIP FORMULATIONS WITH GUAR GUM

| Ingredients | Compounds/commercial refs. | Example 5 according to the invention (weight %) | Example 6 according to the invention (weight %) |
|---|---|---|---|
| Dispersion of ethylcellulose in water | Ethylcellulose at 26.2% in water; sodium lauryl sulfate (1.3%) and cetyl alcohol (2.5%) Aquacoat ECD 30 from FMC Biopolymer | 32.97* | 32.97* |
| Nonvolatile oil | Octyldodecanol | 32.97 | 32.97 |
| Nonvolatile silicone oil | Triméthylsiloxyphényl diméthicone/BELSIL PDM 1000 de Wacker | 23 | — |
|  | Diméthicone (Wacker-Belsil DM 350 de Wacker) | — | 23 |
| Non volatile oil | Dimethicone (Wacker-Belsil DM 350 from Wacker) | 23 | 23 |
| Thickener | Guar gum | 0.2 | 0.2 |
| Preservatives | Phenoxyethanol and ethanol | 3.5 | 3.5 |
| Solvent | Water | 3.06 | 3.06 |
| Thickener | Polyvinyl alcohol | 0.5 | 0.5 |
| Surfactant | Mixture of sorbitan stearate and sucrose cocoate (Arlatone 2121U from Croda) | 4 | 4 |
| Water-soluble dyes | Disodium salt of fuchsin acid D (CI: 17200), disodium salt of tartrazine (CI: 19140) and trisodium salt of Allura Red (CI: 16035) | 0.3 | 0.3 |
|  | Total: | 100 | 100 |

*Expressed as weight of commercial product.

Preparation Protocol
1) The aqueous dispersion of ethylcellulose is mixed with the nonvolatile oil with stirring, and the mixture is heated for 1 to 2 hours at 55° C.
2) The surfactant is added and the mixture is stirred at 55° C. until homogeneous.
3) The guar gum is added until a homogeneous mixture is obtained, and the resulting mixture is left to cool to room temperature.
4) The nonvolatile silicone oil is then added with continued stirring.
5) The dyes predissolved in water are then added.
6) Finally, the alcohol and the phenoxyethanol are added with stirring.

Result:

After 24 hours, the compositions of Example 6 and 7 has the appearance of a very fluid homogeneous cream. Under microscope observation, the compositions have the aspect of a clean homogeneous dispersion. The application of the compositions on the lips is easy and comfortable. The compositions produce a glossy uniform makeup on the lips and have a satisfactory level of wear property of the color.

EXAMPLES 7 TO 9: INFLUENCE OF STABILIZING/THICKENING AGENTS

|  |  | Example 7 according to the invention (% en poids) | Example 8 according to the invention (% en poids) | Example 9 according to the invention (% en poids) |
| --- | --- | --- | --- | --- |
| Dispersion of ethylcellulose in water | Ethylcellulose à 26.2% dans l'eau; lauryl sulfate de sodium (1.3%) et alcool cétylique (2.5%) AQUACOAT ECD 30 de FMC Biopolymer | 32.97* | 32.97* | 32.97* |
| Nonvolatile oil | Octyldodécanol | 32.97 | 32.97 | 32.97 |
| Thickener | Gomme de guar | 0.2 | — | 0.2 |
| Surfactant | Mélange de stéarate de sorbitane, cocoate de sucrose (Arlatone 2121U de Croda) | 4 | 4 | — |
| Solvent | Eau | 3.36 | 3.56 | 7.36 |
| Non-volatile silicone oil | Triméthylsiloxyphényl diméthicone/BELSIL PDM 1000 de Wacker | 23 | 23 | 23 |
| Preservatives | Phénoxy éthanol et éthanol | 3.5 | 3.5 | 3.5 |
|  | TOTAL | 100 | 100 | 100 |

*Exprimée en poids de produit commercial.

Preparation Protocol
1) The aqueous dispersion of ethylcellulose is mixed with the nonvolatile oil with stirring, and the mixture is heated for 1 to 2 hours at 55° C.
2) The surfactant is added and the mixture is stirred at 55° C. until homogeneous (EX7 and EX8).
3) The guar gum is added (EX7 and EX9) until a homogeneous mixture is obtained, and the resulting mixture is left to cool to room temperature.
4) The nonvolatile silicone oil is then added with continued stirring.
5) The dyes predissolved in water are then added.
6) Finally, the alcohol and the phenoxyethanol are added with stirring.

Result:

After 24 hours, the compositions of Example 7 has the appearance of a very fluid homogeneous cream, the composition of Example 8 the appearance of a milk quite homogeneous, and the composition of Example 9 the appearance of a milk quite homogenous. Under microscope observation, the compositions have the aspect of a clean homogeneous dispersion. The application of the compositions on the lips is easy and comfortable. The compositions produce a glossy uniform makeup on the lips and have a satisfactory level of wear property of the color.

EXAMPLES 10 AND 11

| | Liquid lip formulations | | |
|---|---|---|---|
| Ingredients | Compounds/commercial refs. | Example 10 according to the invention (weight %) | Example 11 According to the invention (weight %) |
| Dispersion of ethylcellulose in water | Ethylcellulose at 26.2% in water; sodium lauryl sulfate (1.3%) and cetyl alcohol (2.5%) Aquacoat ECD 30 from FMC Bioplymer | 32.97* | 32.97* |
| Nonvolatile oil | Octyldodecanol | 32.97 | 32.97 |
| Non volatile oil | Trimethylsiloxyphenyl dimethicone/Belsil PDM 1000 from Wacker | 11.5 | — |
| | Dimethicone (Wacker-Belsil DM 350 from Wacker) | | 11.5 |
| | Dimethicone (Mirasil 500 000 from Bluestar) | 11.5 | 11.5 |
| Preserving agents | Phenoxyethanol and ethanol | 3.5 | 3.5 |
| Solvent | Water | 3.26 | 3.26 |
| Surfactant | Mixture of sorbitan stearate and sucrose cocoate (Arlatone 2121U from Croda) | 4 | 4 |
| Dyestuffs | Red 33 | 0.135 | 0.135 |
| | Yellow 5 | 0.045 | 0.045 |
| | Red 40 | 0.12 | 0.12 |
| | Total | 100 | 100 |

*Expressed as weight of commercial product.

Preparation Protocol
1) The aqueous dispersion of ethylcellulose is mixed with the nonvolatile polar oil with stirring, and the mixture is heated for 1 to 2 hours at 55° C.
2) The surfactant is added and the mixture is stirred at 55° C. until homogeneous.
3) The Dimethicone (Mirasil 500 000 from Bluestar) and the Polyphenyltrimethylsiloxy dimethylsiloxane (Wacker-Belsil PDM 1000 from Wacker) (Example 6) or the Dimethicone (Wacker-Belsil DM 350 from Wacker) (Example 7) is homogenized at room temperature.
4) The mixture thus obtained is then added to the mixture containing the ethylcellulose, with continued stirring.
5) The dyes/pigments predissolved in water are then added.
6) Finally, the alcohol and the phenoxyethanol are added with stirring.

Evaluation of the Formulas

The tacky aspect of each of the formulas thus obtained was evaluated according to the protocol defined below.

Protocol for Evaluating the Tack

A sample of each of the compositions was spread while hot onto a contrast card so as to form a film 150 µm thick. The tacky nature on the finger was evaluated during drying of the formula after one hour and 24 hours at room temperature (25° C.). To do this, a finger was applied, after the specified drying time, onto the applied formula and the tack was assessed by the person on removal of their finger from the applied formula.

The aspect of the composition and the aspect of the deposit, and also the gloss properties of the deposit, were also evaluated.

Result

A fluid, airy mixture is obtained for the compositions of Examples 10 and 11.

The compositions of Examples 10 and 11 are applied to the lips. They are comfortable on application (easy to apply and glide on application) and the deposits obtained are slightly tacky.

For each of the compositions of Examples 10 and 11, the makeup deposits obtained are thin and light, have very good gloss and gloss remanence (especially over 1 hour) on the lips, and also a satisfactory wear property of the color.

For the composition of Example 10, the mixture obtained is more homogeneous than for the composition of Example 11, for which the texture is slightly granular.

EXAMPLES 12 AND 13

| | Liquid lip formulations | | |
|---|---|---|---|
| Ingredients | Compounds/Commercial refs. | Example 12 according to the invention (weight %) | Example 13 according to the invention (weight %) |
| Dispersion of ethylcellulose in water | Ethylcellulose at 26.2% in water; sodium lauryl sulfate (1.3%) and cetyl alcohol (2.5%)/ Aquacoat ECD 30 from FMC Biopolymer | 32.97* | 32.97* |
| Nonvolatile oil | Octyldodecanol | 32.97 | 32.97 |
| Solvent | Water | 3.26 | 3.26 |
| Surfactant | Mixture of sorbitan stearate, sucrose cocoate/Arlatone 2121U from Croda | 4 | 4 |

-continued

| | | Liquid lip formulations | | |
|---|---|---|---|---|
| Ingredients | Compounds/Commercial refs. | | Example 12 according to the invention (weight %) | Example 13 according to the invention (weight %) |
| Dyestuffs | Red 33 | | 0.135 | 0.135 |
| | Yellow 5 | | 0.045 | 0.045 |
| | Red 40 | | 0.12 | 0.12 |
| Silicone oil | Polyphenyltrimethylsiloxydimethylsiloxane (viscosity: 1000 cSt- MW: 3000 g/mol)/ Wacker-Belsil PDM 1000 from Wacker | | 11.5 | — |
| | Dimethicone (Wacker-Belsil DM 350 from Wacker) | | — | 11.5 |
| Organopolysiloxane elastomer | Dimethicone (and) dimethicone/vinyl dimethicone crosslinked polymer (KSG 16 from Shin-Etsu) | | 11.5 | 11.5 |
| Preserving agent | Phenoxyethanol and ethanol | | 3.5 | 3.5 |
| | Total | | 100 | 100 |

*Expressed as weight of commercial product.

Preparation Protocol
1) The aqueous dispersion of ethylcellulose is mixed with the nonvolatile polar oil with stirring, and the mixture is heated for 1 to 2 hours at 55° C.
2) The surfactant is added and the mixture is stirred at 55° C. until homogeneous.
3) The organopolysiloxane elastomer and the Polyphenyltrimethylsiloxy dimethylsiloxane (Wacker-Belsil PDM 1000 from Wacker) (Example 8) or the Dimethicone (Wacker-Belsil DM 350 from Wacker) (Example 9) is homogenized at room temperature.
4) The mixture thus obtained is then added to the mixture containing the ethylcellulose, with continued stirring.
5) The dyes/pigments predissolved in water are then added.
6) Finally, the alcohol and the phenoxyethanol are added with stirring.

Evaluation of the Formulas

The tacky aspect, the aspect of the composition, the aspect of the deposit, and the gloss properties of the deposit were evaluated for each of the formulas thus obtained, according to the protocol described in Examples 10 and 11.

Result

A fluid, homogeneous mixture is obtained for the compositions of Examples 12 and 13.

The compositions of Examples 12 and 13 are applied to the lips. They are comfortable on application (easy to apply and glide on application) and the deposits obtained are not tacky.

For each of the compositions of Examples 12 and 13, the makeup deposits obtained are homogeneous, thin and light, have very good gloss and gloss remanence (especially over 1 hour) on the lips, and also a satisfactory wear property of the color.

EXAMPLES 14 TO 16

Preparation of the MQTpr Siloxane Resins

The following resins are used:

MQ resin=an MQ resin of formula $M^{0.43}Q^{0.57}$ and of Mn=3230 dissolved in xylene to a proportion of 70.8% by weight of solids. The MQ resin was manufactured according to the techniques described by Daudt in U.S. Pat. No. 2,676,182.

T Propyl resin=a propyl silsesquioxane resin at 74.8% by weight in toluene. The propyl silsesquioxane resin was obtained by hydrolysis of propyltrichlorosilane.

Preparation of the $MQT^{Pr}$ Resins

An MQ resin, a T propyl resin, xylene and 1M KOH in water in the proportions presented in Table 1 are introduced into a 3-necked flask equipped with a stirrer, a temperature probe and Dean-Stark apparatus mounted with a condenser. Xylene is pre-introduced into the Dean-Stark apparatus so as to ensure maintenance of a level of solids of 50% in the reactor. The mixture in the reactor is refluxed (between 100 and 140° C.) for at least 3 hours. Any water formed in the reaction mixture is continuously removed and trapped in the form of an azeotrope in the Dean-Stark apparatus. After refluxing for 3 hours, the water is removed from the apparatus and heating is continued for a further 30 minutes. After cooling the mixture, an excess of acetic acid is added to neutralize the KOH in the mixture. The mixture is then filtered to remove the salts formed, by passing it through a filter under pressure. Solvent exchange is performed by heating the mixture in a rotary evaporator under vacuum. After removing the majority of the xylene, decamethylcyclopentasiloxane (or isododecane) is added while continuing to remove any residual aromatic solvent. The structures of the resulting siloxane resins are characterized by $^{29}$Si NMR spectroscopy and GPC, and the results are summarized in Table 2 below.

TABLE 1

| Example | Mass ratio of MQ/ $T^{Pr}$ resins added | Weight % of MQ resin | Weight % of T propyl resin | Weight % of xylene | Weight % of 1M KOH | Weight % of acetic acid |
|---|---|---|---|---|---|---|
| 1-a | (85/15) | 59.4 | 10.5 | 29.1 | 0.9 | 0.2 |
| 1-b | (50/50) | 34.9 | 34.8 | 29.1 | 0.9 | 0.2 |
| 1-c | (30/70) | 20.9 | 48.8 | 29.2 | 0.9 | 0.2 |
| 1-d | (95/5) | 67.1 | 3.5 | 28.3 | 0.9 | 0.2 |
| 1-e | (100/0) | 69.3 | 0 | 28.8 | 0.9 | 0.2 |

TABLE 2

| Example | Resin structure according to NMR characterization | Weight % of OH | Mn | Mw | Mw/Mn |
|---|---|---|---|---|---|
| MQ Resin | $M^{0.43}Q^{0.57}$ | | 3230 | 1516 | 4.7 |
| T Propyl resin | $T^{Pr}_{1.0}$ | 7.0 | 3470 | 11 400 | 3.3 |
| 1-a | $M_{0.374}Q_{0.529}{:}T^{Pr}_{0.097}$ | 1.4 | 5880 | 271 000 | 46.1 |
| 1-b | $M_{0.248}Q_{0.341}{:}T^{Pr}_{0.412}$ | 2.1 | 6640 | 3 860 000 | 581.3 |
| 1-c | $M_{0.162}Q_{0.217}{:}T^{Pr}_{0.621}$ | 1.5 | 7600 | 25 300 000 | 3329 |
| 1-d | $M_{0.419}Q_{0.5485}{:}T^{Pr}_{0.03}$ | 1.5 | | | |
| 1-e | MQ | 1.7 | 5200 | 28 900 | 5.6 |

Examples of Liquid Lip Formulations

| Ingredients | Compounds/commercial refs. | Example 14 according to the invention (weight %) | Example 15 According to the invention (weight %) | Example 16 (according to the invention) (weight %) |
|---|---|---|---|---|
| Dispersion of ethylcellulose in water | Ethylcellulose at 26.2% in water; sodium lauryl sulfate (1.3%) and cetyl alcohol (2.5%) Aquacoat ECD 30 from FMC Biopolymer | 32.97* | 32.97* | 32.97* |
| Nonvolatile oil | Octyldodecanol | 32.97 | 32.97 | 32.97 |
| Solvent | Water | 3.26 | 3.26 | 3.26 |
| Surfactant | Mixture of sorbitan stearate and sucrose cocoate (Arlatone 2121U from Croda) | 4 | 4 | 4 |
| Dyestuffs | Red 33 | 0.135 | 0.135 | 0.135 |
| | Yellow 5 | 0.045 | 0.045 | 0.045 |
| | Red 40 | 0.12 | 0.12 | 0.12 |
| Nonvolatile oil | Trimethylsiloxyphenyl dimethicone/Belsil PDM 1000 from Wacker | 20.5 | — | — |
| | Dimethicone (Wacker-Belsil DM 350 from Wacker) | — | 20.5 | 11.5 |
| | Trimethyl siloxysilicate resin (SR 1000 from Momentive Performance Materials) | 2.5 | 2.5 | — |
| Silicone resin | MQ-T propyl resin (30/70) at 701.3% in isododecane, as prepared in Example 1-C above | | | 11.5 (7.18% active material in 4.32% of isododecane) |
| Preserving agent | Phenoxyethanol and ethanol | 3.5 | 3.5 | 3.5 |
| | Total | 100 | 100 | 100 |

*Expressed as weight of commercial product.

Preparation Protocol

1) The aqueous dispersion of ethylcellulose is mixed with the nonvolatile polar oil with stirring, and the mixture is heated for 1 to 2 hours at 55° C.
2) The surfactant is added and the mixture is stirred at 55° C. until homogeneous.
3) The silicone resin is dispersed in the Polyphenyltrimethylsiloxy dimethylsiloxane (Wacker-Belsil PDM 1000 from Wacker) (Example 11) or in the Dimethicone (Wacker-Belsil DM 350 from Wacker) (Examples 12 and 13) at room temperature.
4) The mixture thus obtained is then added to the mixture containing the ethylcellulose, with continued stirring.
5) The dyes/pigments predissolved in water are then added.
6) Finally, the alcohol and the phenoxyethanol are added with stirring.

Evaluation of the Formulas

The tacky aspect, the aspect of the composition, the aspect of the deposit, and the gloss properties of the deposit were evaluated for each of the formulas thus obtained, according to the protocol described in Examples 10 and 11.

Result

A fluid, homogeneous mixture is obtained for the compositions of Examples 14, 15 and 16.

The compositions of Examples 14, 15 and 16 are applied to the lips. They are comfortable on application (easy to apply and glide on application) and the deposits obtained are not tacky.

For each of the compositions of Examples 14, 15 and 16, the makeup deposits obtained are homogeneous, thin and light, have very good gloss and gloss remanence (especially over 1 hour) on the lips, and also a satisfactory wear property of the color.

The invention claimed is:

1. A cosmetic composition, for making up and/or caring for the lips, comprising, in a physiologically acceptable medium:

(a) an aqueous phase comprising at least 15% by weight of water;
(b) at least one ethyl cellulose; said ethylcellulose being present in a content of between 1% and 60% by weight relative to the total weight of the composition;
(c) 10% to 50% by weight relative to the total weight of the composition of at least one first hydrocarbon-based non-volatile oil liquid at room temperature, where room temperature is 25° C., and atmospheric pressure, where atmospheric pressure is 760 mmHg, said at least one first hydrocarbon-based non-volatile oil being octyldodecanol;
(d) at least one second non-volatile oil that is a liquid at room temperature, where room temperature is 25° C., and atmospheric pressure, where atmospheric pressure is 760 mmHg, selected from apolar hydrocarbon-based oils having a solubility parameter at 25° C., δa, of the at least one second non-volatile oil is equal to 0 $(J/cm^3)^{1/2}$, said apolar hydrocarbon based oils being selected from the group consisting of liquid paraffin, liquid petroleum jelly, polybutylenes, hydrogenated polyisobutylenes, decene/butene copolymers, polybutene/polyisobutene copolymers, polydecenes and hydrogenated polydecenes, and mixtures thereof;

(e) at least one stabilizer that is a surfactant and/or a hydrophilic gelling agent; and (f) at least one dyestuff selected from the group consisting of organic pigments, composite pigments, and mixtures thereof, wherein the composition comprises from 45% to 75% by weight of non-volatile oils, wherein the composition is stable and homogeneous, wherein the composition further comprises at least one monoalcohol containing from 1 to 5 carbon atoms, and wherein the dyestuff is present in an amount sufficient to produce a colored optical effect upon application to the lips sufficient to make up the lips.

2. The composition according to claim 1, wherein the stabilizer is at least one nonionic or anionic surfactant.

3. The composition according to claim 1, wherein the surfactant is at least sodium lauryl sulfate.

4. The composition according to claim 1, wherein the composition is in the form of an oil-in-water emulsion.

5. The composition according to claim 1, wherein the composition comprises (i) the surfactant in a content ranging from 0.1% to 20% by weight relative to the total weight of the composition, and/or (ii) the hydrophilic gelling agent in a content ranging from 0.1% to 10% by weight relative to the total weight of the composition.

6. The composition according to claim 1, comprising the second non-volatile oil in a content ranging from 10% to 45% by weight relative to the total weight of the composition.

7. The composition according to claim 1, wherein a weight ratio of the first hydrocarbon-based non-volatile oil to the ethylcellulose is between 1 and 20.

8. The composition according to claim 1, comprising between 15% and 80% by weight of water relative to the total weight of the composition.

9. The composition according to claim 1, comprising: from 4% to 30% by weight of ethylcellulose, and from 15% to 50% by weight of water.

10. The composition according to claim 1, further comprising at least one compound chosen from fillers, waxes, pasty fatty substances, semicrystalline polymers, lipophilic gelling agents, silicone gums, organopolysiloxane elastomers, silicone resins, and mixtures thereof.

11. The composition according to claim 1, wherein the composition is in liquid form.

12. A cosmetic process for making up and/or caring for the lips, comprising applying to the lips at least the composition according to claim 1.

13. The composition according to claim 1, wherein the nonvolatile apolar hydrocarbon-based oils are free of oxygen atoms.

14. The composition according to claim 1, wherein the composition is free of silicone surfactant.

15. The composition according to claim 1, wherein the second nonvolatile oil is selected from the group consisting of polydecene, hydrogenated polydecene, and mixtures thereof.

16. The composition according to claim 1, wherein the aqueous phase comprises from 15% to 80% by weight of water.

17. The composition according to claim 1, wherein the ethylcellulose used during preparation of the composition is in the form of particles dispersed in an aqueous phase.

* * * * *